United States Patent
Vachtsevanos et al.

(10) Patent No.: US 6,269,179 B1
(45) Date of Patent: *Jul. 31, 2001

(54) INSPECTION SYSTEM AND METHOD FOR BOND DETECTION AND VALIDATION OF SURFACE MOUNT DEVICES USING SENSOR FUSION AND ACTIVE PERCEPTION

(75) Inventors: George J. Vachtsevanos, Marietta, GA (US); Iqbal M. Dar, Odenton, MD (US)

(73) Assignee: Georgia Tech Research Corporation, Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/093,685

(22) Filed: Jun. 9, 1998

Related U.S. Application Data

(60) Division of application No. 08/753,181, filed on Nov. 20, 1996, now Pat. No. 5,963,662, and a continuation-in-part of application No. 08/657,023, filed on May 31, 1996, now Pat. No. 5,815,198.
(60) Provisional application No. 60/023,519, filed on Aug. 7, 1996.

(51) Int. Cl.$^7$ ..................................................... G06K 9/00
(52) U.S. Cl. .......................... 382/149; 382/159; 382/227; 348/126
(58) Field of Search ..................................... 382/141, 142, 382/143, 144, 145, 146, 147, 148, 149, 150, 224, 225, 226, 227, 228, 155, 156, 157, 159, 160; 348/164, 87, 126, 131, 166, 165, 88; 356/51, 372, 237; 364/468.17, 557

(56) References Cited

U.S. PATENT DOCUMENTS

| | | | |
|---|---|---|---|
| 3,795,918 | 3/1974 | Sunderland | 356/45 |
| 5,115,475 | 5/1992 | Lebeau . | |
| 5,544,256 | * 8/1996 | Brecher et al. | 382/149 |
| 5,621,811 | * 4/1997 | Roder et al. | 382/147 |
| 5,815,198 | * 9/1998 | Vachtsevanos et al. | 348/88 |
| 5,835,633 | * 11/1998 | Fujisaki et al. | 382/187 |

OTHER PUBLICATIONS

Mike Juha, "X–Ray Machine Vision For Circuity Board Inspection," pp. 3–41–3–55.

Riccardo Vanzetti et al., "Combining Soldering With Inspection," Oct. 1988, pp. 29–32.

L.A. Zadeh, "Fuzzy Sets As A Basic For A Theory Of Possibility," Feb. 1977, pp. 3–29.

David W. Capson et al., "A Tiered–Color Illumination Approach For . . . Joints," May 1988, pp. 387–393.

(List continued on next page.)

Primary Examiner—Joseph Mancuso
Assistant Examiner—Vikkram Bali
(74) Attorney, Agent, or Firm—Thomas, Kayden, Horstemeyer & Risley

(57) ABSTRACT

A hybrid surface mount component inspection system which includes both vision and infrared inspection techniques to determine the presence of surface mount components on a printed wiring board, and the quality of solder joints of surface mount components on printed wiring boards by using data level sensor fusion to combine data from two infrared sensors to obtain emissivity independent thermal signatures of solder joints, and using feature level sensor fusion with active perception to assemble and process inspection information from any number of sensors to determine characteristic feature sets of different defect classes to classify solder defects.

15 Claims, 27 Drawing Sheets

OTHER PUBLICATIONS

Sandra L. Bartlett et al., "Automatic Solder Joint Inspection," Jan. 1988, pp. 31–43.

Kenneth Reid, "Automated Soldering Inspection Technology Study," pp. 1288–1297.

G. Hamid, "An FPGA–Based Coprocessor For Image Processing," IEE Colloq. (1994), pp. 6/1–6/4.

J. Rose et al., "Architecture Of Field–Programmable Gate Arrays . . . Efficiency," Oct. 1990, pp. 1217–1225.

Dennis Lazaroff et al., "Evaluating Different Sampling Techniques . . . Systems," IEEE (1991), pp. 92–97.

Roger Z. Lui et al., "Infrared Solder Joint Inspection On Surface Mount . . . Boards," IEEE(1996), pp. 145–148.

Dar et al., "Bond Validation Of Surface Mount Components Using A Combined IR/ Vision System," pp. 1–7.

L. Zadeh, "Outline Of A New Approch To The Analysis Of Complex . . . Processes," Jan. 1973, pp. 28–44.

* cited by examiner

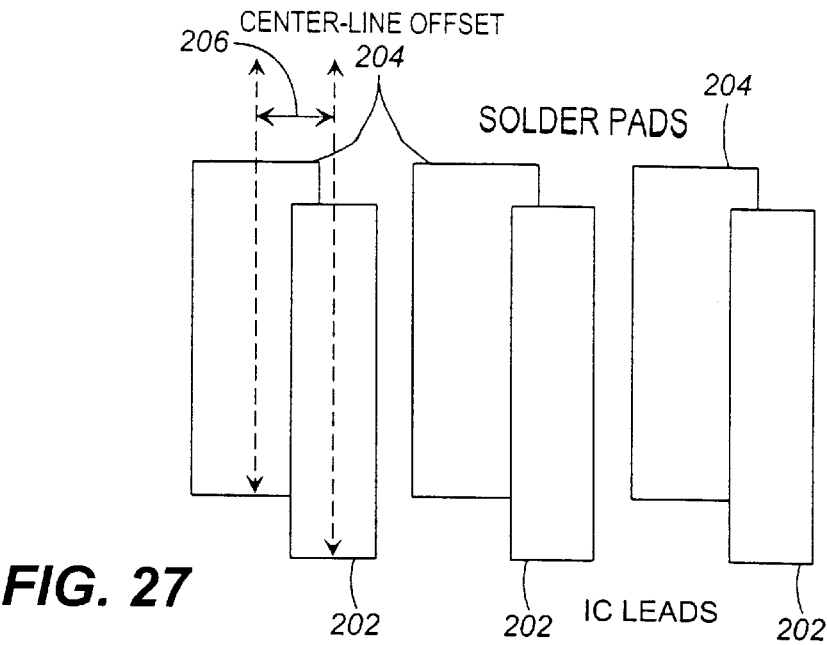

FIG. 27

BOND VALIDATION OF SURFACE MOUNT DEVICES
GEORGIA INSTITUTE OF TECHNOLOGY - PROJECT RESEARCH LAB

BOND VALIDATION: MAIN MENU

A-) REINITIALIZE AD1000'S

C-) CREATE A NEW FILE

O-) OPEN EXISTING FILE

I-) INITIALIZE THE TABLE

R-) REVIEW FILE

T-) TEACH POSITIONS

N-) INFRARED ANALYSIS

V-) VISION ANALYSIS

M-) IMAGE CAPTURE

P-) PLOT DATA/IMAGES

D-) DISPLAY TIF FORMAT CAPTURED IMAGE

E-) EDIT AS TEXT FILE

Q-) QUIT

CHOOSE BY LETTER:

FILE: <NONE>

FIG. 28

INSPECTION SYSTEM AND METHOD FOR BOND DETECTION AND VALIDATION OF SURFACE MOUNT DEVICES USING SENSOR FUSION AND ACTIVE PERCEPTION

CROSS REFERENCE TO RELATED APPLICATION

This application is a continuation-in-part of application Ser. No. 08/657,023, filed on May 31, 1996, now U.S. Pat. No. 5,815,198, and is a divisional of application Ser. No. 08/753,181, filed Nov. 20, 1996, now U.S. Pat. No. 5,963, 662, which claims benefit of the filing date of previously filed provisional application entitled INSPECTION SYSTEM AND METHOD FOR BOND DETECTION AND VALIDATION OF SURFACE MOUNT DEVICES, Ser. No. 60/023,519, filed Aug. 7, 1996.

FIELD OF THE INVENTION

The present invention relates generally to quality control inspection systems and more particularly, to an inspection system and method for bond detection and validation of surface mount devices using vision and infrared sensors, combined with a technique for discriminating and detecting solder joint defects.

BACKGROUND OF THE INVENTION

It is indeed paradoxical that, on one hand, the quality of manufactured printed circuit boards (PCBs) has increased steadily over the past years while, on the other hand, the need for quality assurance has become more pronounced. As packaging technology marches on from through hole to surface mount to multichip modules, the complexity and sophistication of these processes introduce a larger aggregation of defect categories and impose stringent performance requirements The critical role of electronic devices in diverse application areas such as missiles, aircraft, automotive manufacturing, computers and communications, etc. necessitates means for "proof-of-reliability" and metrics of performance. In the case of surface mount technology (SMT), finer pitch leads have increased the complexity of PCBs beyond the point of accurate and repeatable manual inspection. Many studies have been performed that show on a given day, an operator may inspect the same PCB and declare different defects. This lack of reliability and repeatability demands a more accurate approach using automated systems. The most widely used methods for automated inspection are based on vision, infrared (IR),and X-ray. Vision systems are relatively mature but are limited to surface level defects and cannot detect structural defects such as voids. P. J. BesI, et al., "Automated Visual Solder Inspection", *IEEE Transactions on Pattern Analysis Machine Intelligence*, vol. PAMI-11, pp.42–56, March 1985, D. W. Capson and S- K Eng, "A Tried Color Illumination Approach for Machine Inspection of Solder Joints", *IEEE Transactions on Pattern Analysis Machine Intelligence*, vol. PAMI-10, pp.387–393, May 1988 and S. L. Bartlett, et al., "Automatic Solder Joint Inspection," IEEE Transactions on Pattern Analysis Machine Intelligence, vol. PAMI-10, pp.32–42, January 1988. Vanzetti used IR for inspection employing the radiance of the material to determine the mass of solder present. This method is not capable of reliably detecting surface level defects such as linear misalignment and angular misalignment. Riccardo Vanzetti and Alan C. Traub, "Combing Soldering with Inspection", IEEE Control Systems Magazine, pp.29–31, October 1988.

The X-ray based inspection uses radiographic imaging techniques to obtain X-ray images of the solder joints for defect classification. M. Juha, "X-ray Machine Vision for Circuit Board Inspection," *Proceedings of Vision 86 Conf. of SME*, Detroit, Mich., pp.3-41–3-55, June 1986. The X-ray based inspection is reliable in its scope of coverage, but it is very costly and still cannot detect all the defects. The limitations of automated systems are caused by the scope of the individual sensors in classifying the known range of defects. Kenneth Reid, "Automated Soldering Inspection Technology Study," Proceedings of Technology Program of NEPCON West, Anaheim, Calif., vol. 3, pp.1288–1297, February 1993. The complementary nature of IR and vision sensors improves the reliability of the inspection scheme and broadens the scope of quality assurance strategies. The use of multiple sensors requires a system to fuse the information, process it for classification, and ultimately provide feedback to the process. For the system to have practical application, it should be cost effective, and operate in a timely fashion.

A low-cost, robust, flexible and accurate inspection system for detecting and identifying surface mount defects is needed. Inspection requirements vary from one industry sector to another just as the products to be inspected exhibit an enormous range of variability, however there is no universal definition of a good solder joint. In order to meet such diverse requirements, it was decided to design, develop and implement an inspection system that utilizes the synergism and complementarity of vision and IR sensing in a unified platform that may carry out an inspection task on the basis of either 100% testing or a sampled population. The inspection procedure is performed in two stages in order to reduce the inspection time and to have control over the production line delays. The first stage is called a GROSS inspection station that scans a PCB to determine global features to find probable defective areas of the PCB. The second stage is a FINE inspection station that uses intensive methods on questionable areas and generates local features for classification. Since the FINE inspection is performed off-line, it does not create a bottleneck in the production process. The complementary nature of the vision and IR sensors allows a broad range of classifications that would not be possible using only one sensor. This fusion combined with an on-line and off-line inspection procedure, offers a reliable and time efficient system for solder joint inspection.

SUMMARY OF THE INVENTION

A hybrid inspection system which includes vision and IR sensors. The vision sensors are gray scale charge coupled device (CCD) cameras which take 640–480, 256 gray scale 2-dimensional images of the solder joints. The visual inspection techniques include image processing and pattern recognition approaches for automatic inspection of visible defective joints. The IR side of the system uses a laser to heat the joint and observe the IR radiance curve as the joint heats and cools. The IR radiance curve is called a thermal signature of the joint. A two color IR sensor is used to record the thermal signature of a solder joint. The two color IR sensor is used to get emissivity independent thermal signatures by performing data level sensor fusion.

The GROSS inspection station is employed first on-line, to rapidly detect defects such as missing components, angular misalignment, linear misalignment, and solder mass related defects on a sample basis. A vision system checks for the component's presence and for placement related defects. After these defects have been screened, a statistical sampling scheme is used for IR screening to detect defect categories such as excess solder, insufficient solder, no solder and lifted leads. At this stage, the complete thermal signature of the solder joints is captured, but only the difference between starting and peak value, and the difference between peak and final value is analyzed to determine if it falls within normal range. If a potentially defective board is recognized, the candidate PCB is shipped to the FINE inspection station where another vision system captures a higher resolution two-dimensional 256 gray level image of the probable defective areas and exhaustive defect search is performed at the lead level. For the IR inspection, the complete thermal signature, stored at the GROSS inspection station, is analyzed both in the heating and cooling cycles and the defect, if there is one, is declared and classified. The trade-off here is between speed of inspection and thoroughness. The statistical sampling scheme is used to cut down the time required to insect each joint. The sampling rate can be adjusted to meet the constraints of the process. Sensor fusion techniques have been developed to combine vision and IR sensors' data at various levels of abstraction. A data level sensor fusion methodology for two IR sensors provides emissivity independent thermal signatures of the solder joints. At the FINE inspection station, active perception is employed to perform feature level sensor fusion.

Other features and advantages of the present invention will become apparent to one of skill in the art upon review of the following drawings and the detailed description of the preferred embodiments.

BRIEF DESCRIPTION OF THE DRAWINGS

The present invention, as defined in the claims, can be better understood with reference to the following drawings. The drawings are not necessarily to scale, emphasis instead being placed on clearly illustrating principles of the present invention.

FIG. 27 illustrates the centerline offset feature for a linearly misaligned IC.

FIG. 28 illustrates a menu screen of the vision/IR inspection system.

DETAILED DESCRIPTION OF THE PREFERRED EMBODIMENT

Figure 1:
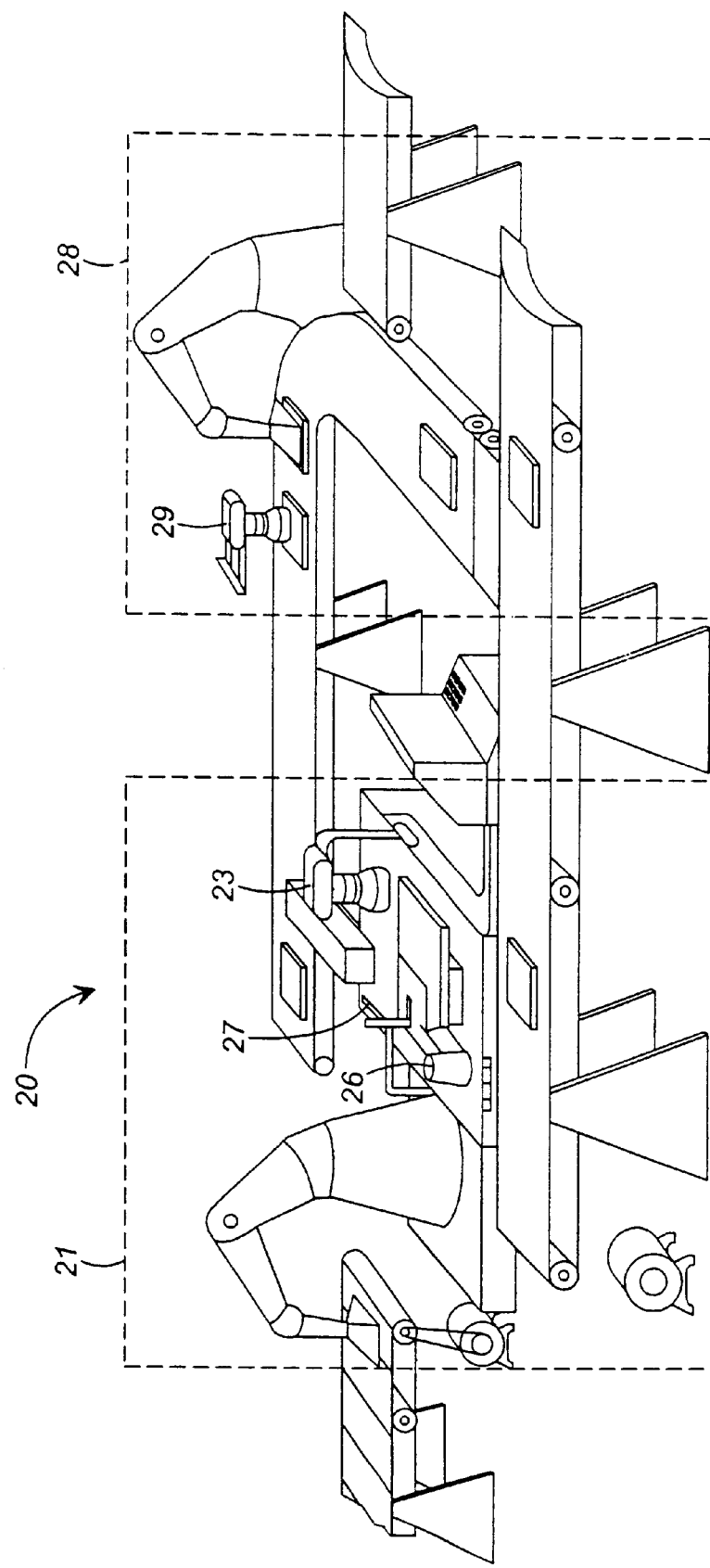
FIG. 1 illustrates the proposed assembly line inspection system for surface mount devices.
Figure 2:
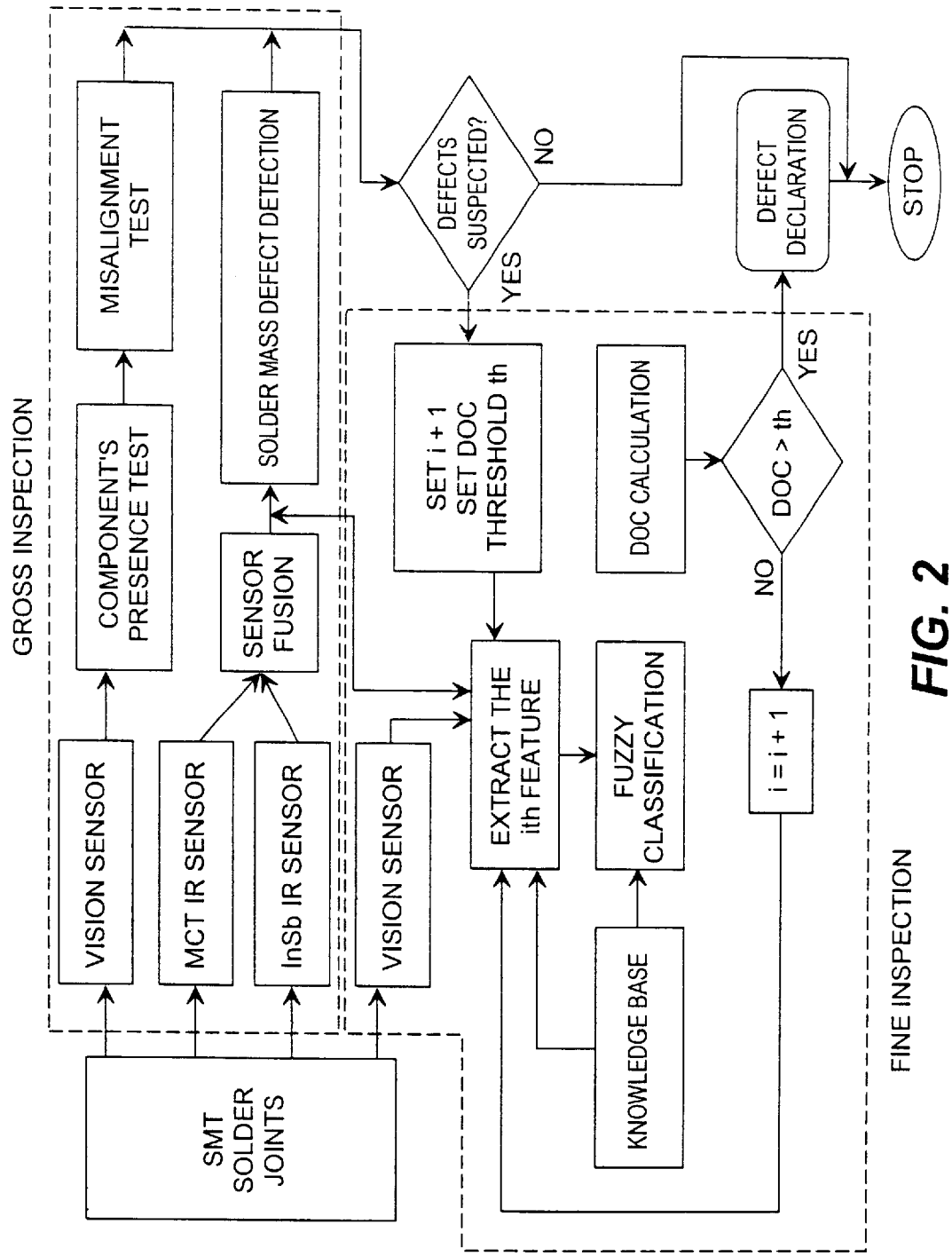
FIG. 2 illustrates the block diagram of combined vision/IR inspection system.

With reference now to the figures wherein like reference numerals designate corresponding parts throughout the several views, FIG. 1 is a view of the proposed assembly line inspection system 20 for surface mount devices and FIG. 2 is a block diagram of the combined vision/IR inspection process. The GROSS inspection station 21 is employed first on-line, to detect missing components, angular misalignment, linear misalignment, and solder mass related defects. A vision system 23 inspects for component presence and placement related defects. Once these defects have been screened, a statistical sampling scheme is used for IR screening to detect defect categories such as excess solder, insufficient solder, no solder and lifted leads. The laser 27 heats the solder joint under inspection while the IR detector 26 captures a complete thermal signature of the solder joint. At this time, only the difference between staring and peak value, and the difference between peak and final value is analyzed to determine if it falls within normal range. If a potentially defective board is recognized, the candidate PCB is shipped to the FINE inspection station 28 where another vision system 29 captures a higher resolution two dimensional 256 gray level image of the probable defective areas and an exhaustive defect search is performed at the lead level. For IR analysis, the complete thermal signature, stored at the GROSS inspection station, is analyzed both in the heating and cooling cycles and the defect, if there is one, is declared and classified. The statistical sampling scheme is used to reduce the time required to inspect each solder joint. The sampling rate can be adjusted to meet the constraints of the process. Sensor fusion techniques have been developed to combine vision and IR sensors' data at various levels of abstraction. A data level sensor fusion methodology for two IR sensors provides emissivity independent thermal signatures of the solder joints. At the FINE inspection station, active perception is employed to perform feature level sensor fusion.

Figure 3:
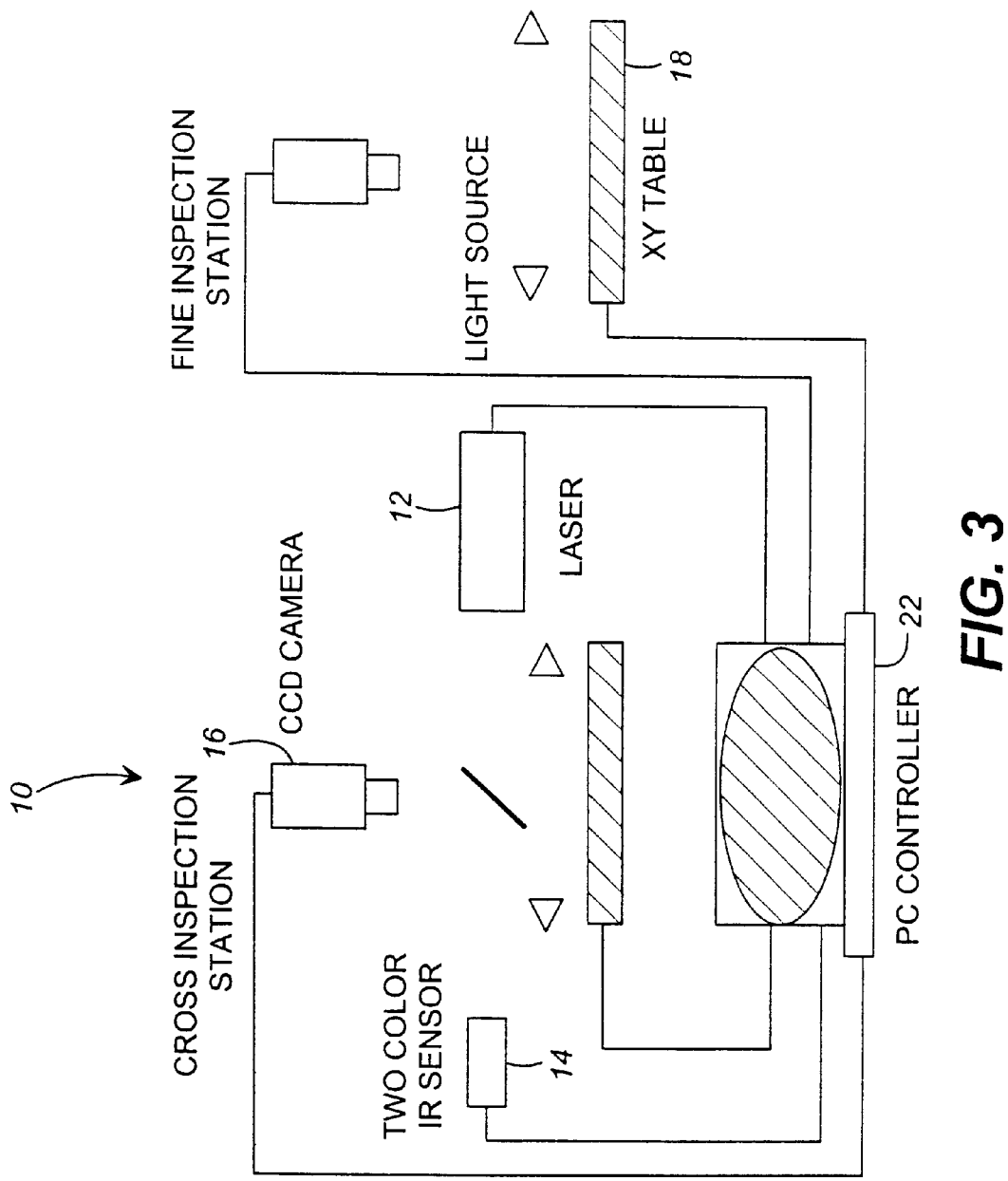
FIG. 3 illustrates the hardware configuration of combined vision/IR inspection system.

FIG. 3 illustrates the principal components of the combined IR/Vision inspection system 10. The experimental setup for the IR inspection utilizes a Nd:YAG 1.06~\µm, 100 W, class IV laser 12 to heat the solder joints, and a two color EG\&G Reticon IR sensor 14 to sense the thermal radiation of the joints. The IR sensors used are Indium Antimonide (InSb) and Mercury-Cadmium-Telluride (MCT), which are sensitive in the 2–5 µm wavelength range and the 6–10 µm range, respectively. The sensor is cooled using liquid nitrogen. Two vision systems are used, one for the GROSS inspection station and one for the FINE inspection station. The GROSS inspection station vision system consists of a ⅔ inch CCD camera 16, a 24 mm telecentric lens, a 9 inch monochrome monitor, and a frame grabber capable of capturing 640×480, 256 gray level images. In general, the solder joint is brighter, and therefore has a higher overall gray scale value than the substrate. The substrate is commonly a shade of green. To assure high quality absorption of the incident light by the substrate, a red-pass filter is used in the illumination. To have uniform shadow free illumination, a circular fiber optics ring light is used. For oblique illumination, a fiber optics goose neck is employed. The FINE inspection station vision system consists of the same setup as that of the GROSS inspection station except for the lens. The lens of FINE inspection station is microscopic lens with variable magnification ratios from 0.7× to 4.5×. An X-Y positioning table 18 with 30 inch travel, is used for moving the PCB under test. The two vision systems, the IR system and X-Y positioning table are controlled by a 90 MHz Pentium based personal computer 22.

GROSS Inspection Software

Figure 4:
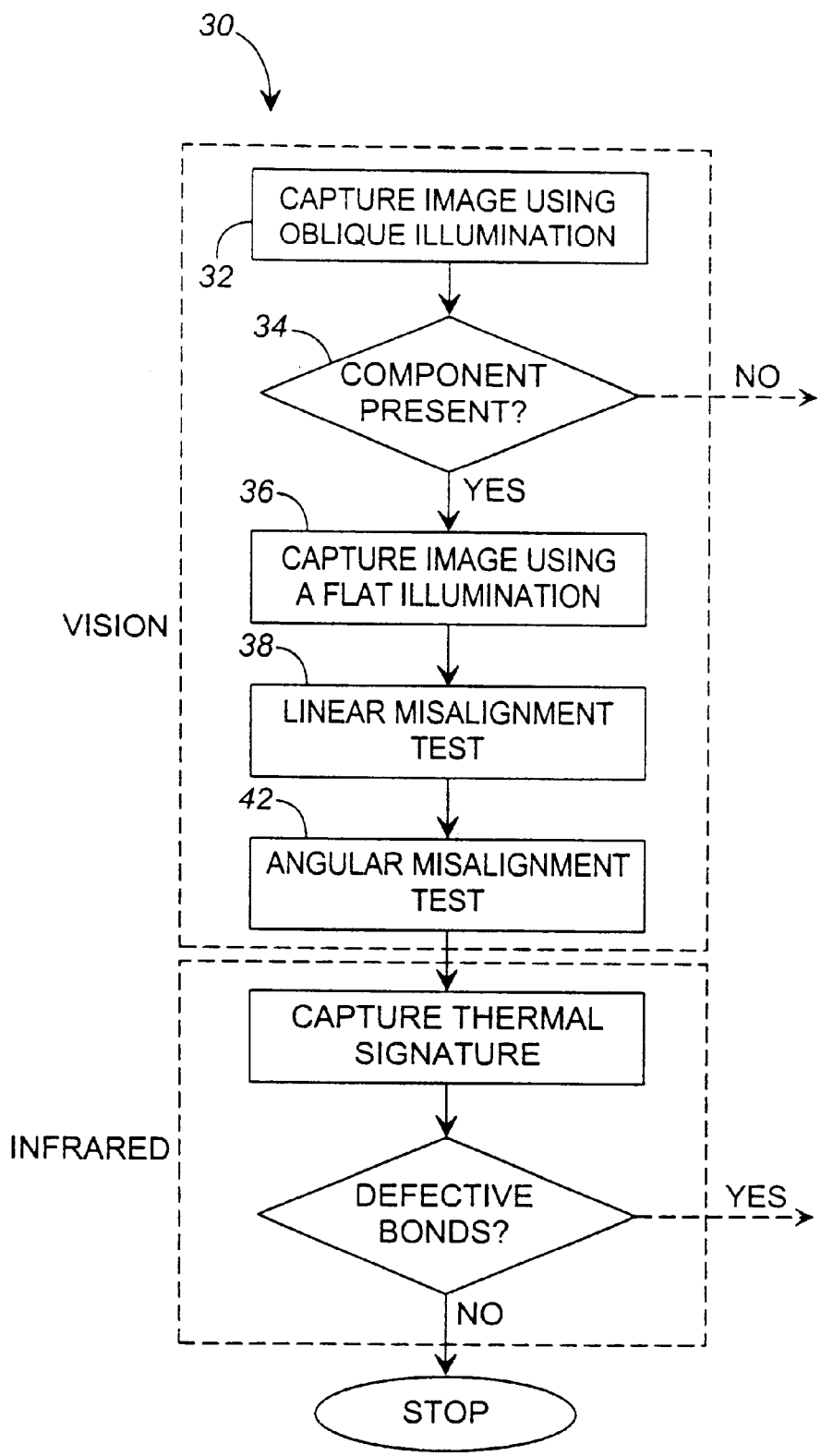
FIG. 4 illustrates the block diagram of GROSS Inspection procedure.

This section details the software developed for the GROSS inspection station. The software has been developed for defect detection and identification, sensor fusion, and control of the overall system. The various preprocessing and recognition modules for the GROSS inspection have been implemented such that they communicate and transfer information sequentially to perform the comprehensive GROSS inspection. FIG. 4 illustrates the flow diagram 30 of the GROSS inspection procedure.

The GROSS inspection station has been designed as a conservative inspection procedure to insure no defective solder joints are declared as good. The defect detection performed at this stage uses vision data and IR thermal signatures in a complementary manner. Since IR can reliably detect the solder mass related defects, it is used to detect the solder mass related defects, such as bridging, excess solder, insufficient solder, cold joint, and lifted leads. The vision GROSS inspection station is used to detect missing components, and component placement related defects such as angular misalignment, and linear misalignment Vision Based GROSS Inspection Referring now to FIG. 4, the vision data system consists of a two-dimensional 256 gray scale image of the PCB. A pattern recognition methodology is employed to detect different types of solder joint defects using these images. Both crisp and fuzzy classifiers have been investigated for defect detection at this stage. The first step in the inspection process of a PCB is to determine whether the components are present on the board 34. Once the component presence is determined, its linear alignment 38 and angular alignment 42 is checked. To perform these tests, two images are captured at each programmed location. These locations are programmed during the off-line training phase. The first image is captured using a directional front illumination technique 32 for the components' presence test. The second image is captured using a diffused front illumination approach 36 for linear and angular misalignment tests.

Component's Presence Test

Figure 5:
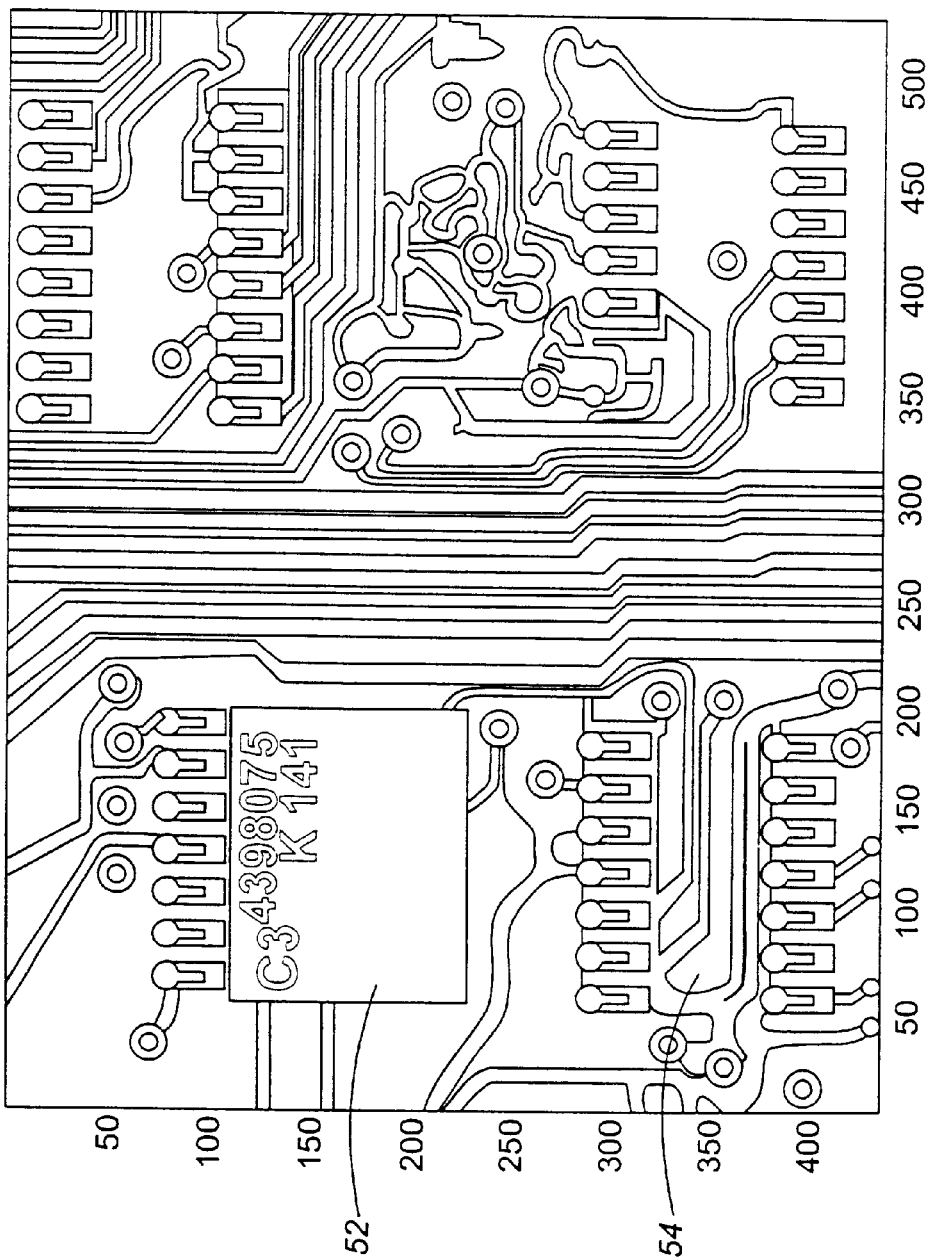
FIG. 5 illustrates a PCB image with directional front illumination.

To detect the component presence and absence efficiently and reliably, features were found that were able to discriminate between the presence and absence of a component. Since the components are three-dimensional objects, while the solder pads underneath are two-dimensional, techniques were considered to exploit this disparity and generate the desired features. Using a directional front illumination technique, the detection of component's presence or absence can be performed effectively and in a timely fashion. The PCB is illuminated by projecting a goose neck halogen light source at approximately 30° from the PCB plane. If the component is present, a shadow is cast. FIG. 5 illustrates the shadow cast by a present component 52 and the lack of a shadow on the missing component 54.

The side of the component toward the light source is called the bright side, and the side with the shadow is called the dark side.

Figure 6:
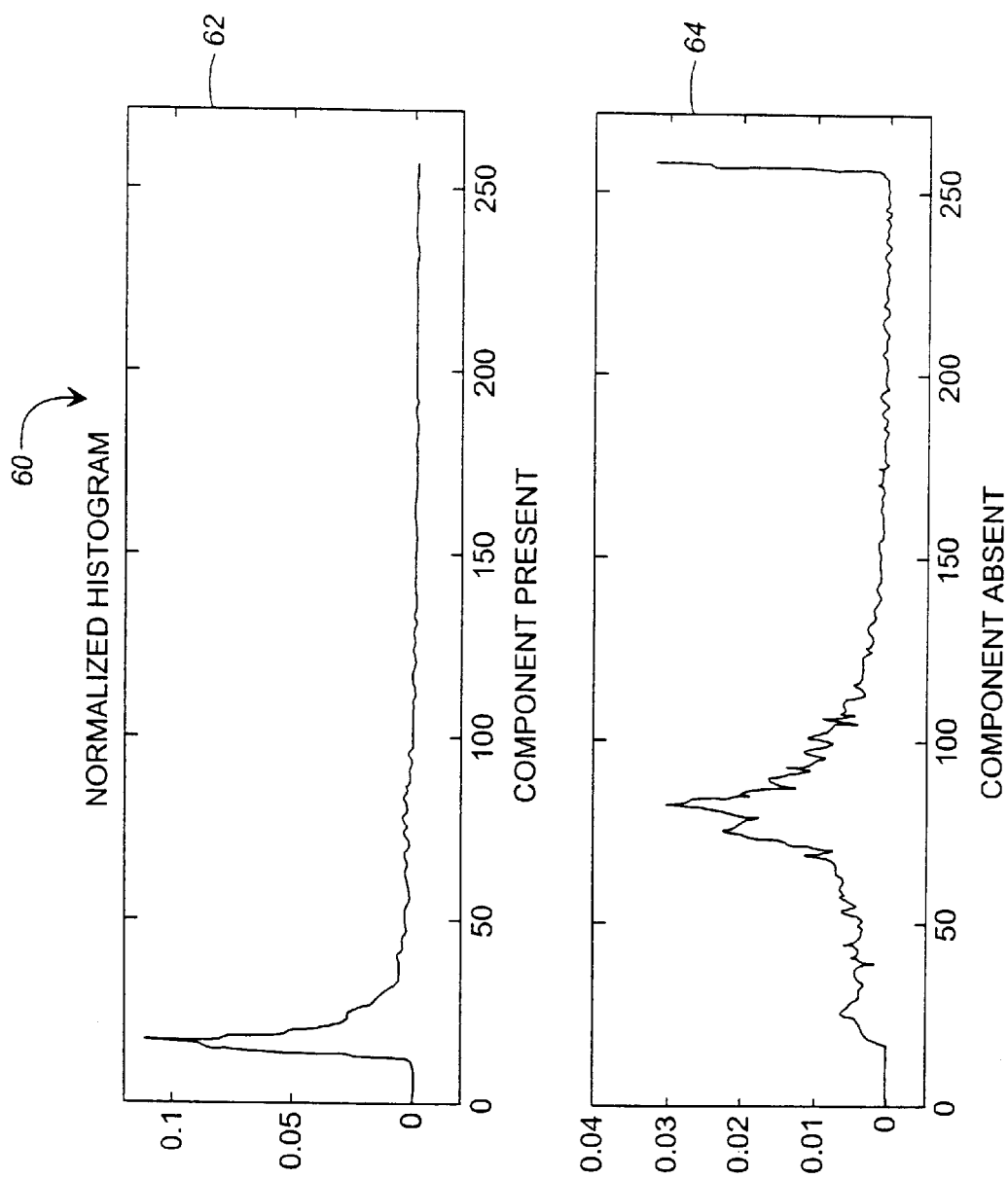
FIG. 6 illustrates histograms of the dark side for component present and absent cases.

Sub-images are extracted by using rectangular windows on all the sides of a component. The windows are defined such that they contain areas specified for the leads of that component. The normalized histogram of each sub-image is calculated and appropriate features are extracted for classification. Referring to FIG. 6, the normalized histogram 60 of the dark side of a component present case 62 and a component absent case 64 are shown.

Figure 7:
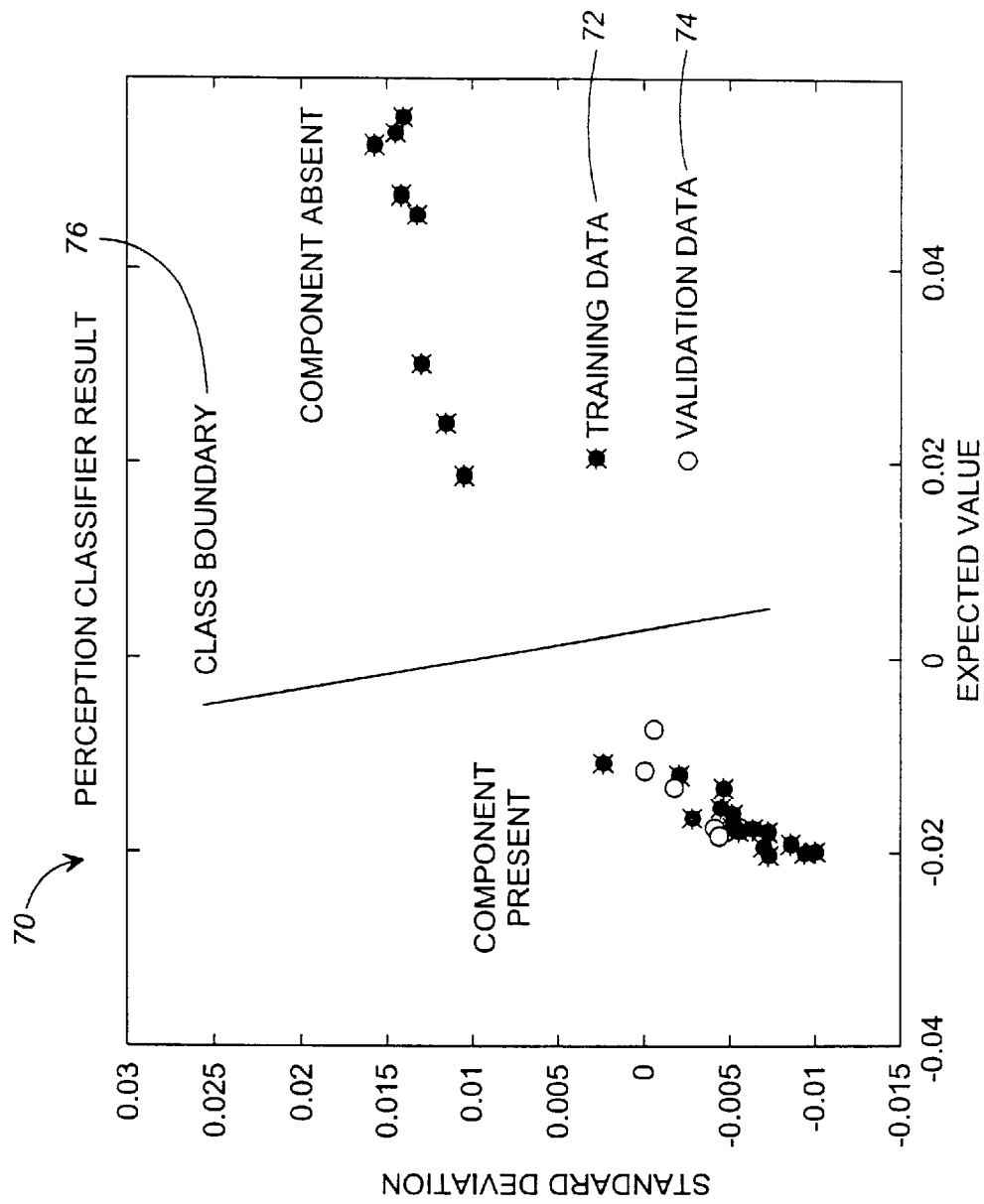
FIG. 7 illustrates perceptron results for component presence test.

The features extracted for component presence test are the expected value and the standard deviation of the normalized histogram. Since the feature space is linearly separable, a perceptron classifier 70 is selected for classification. The training data set for the perceptron consisted of 28 exemplars while the evaluation set consisted of six data values. Referring to FIG. 7, the training data 72, validation data 74 and the class boundary 76 is shown.

Linear Misalignment Test

Figure 8:
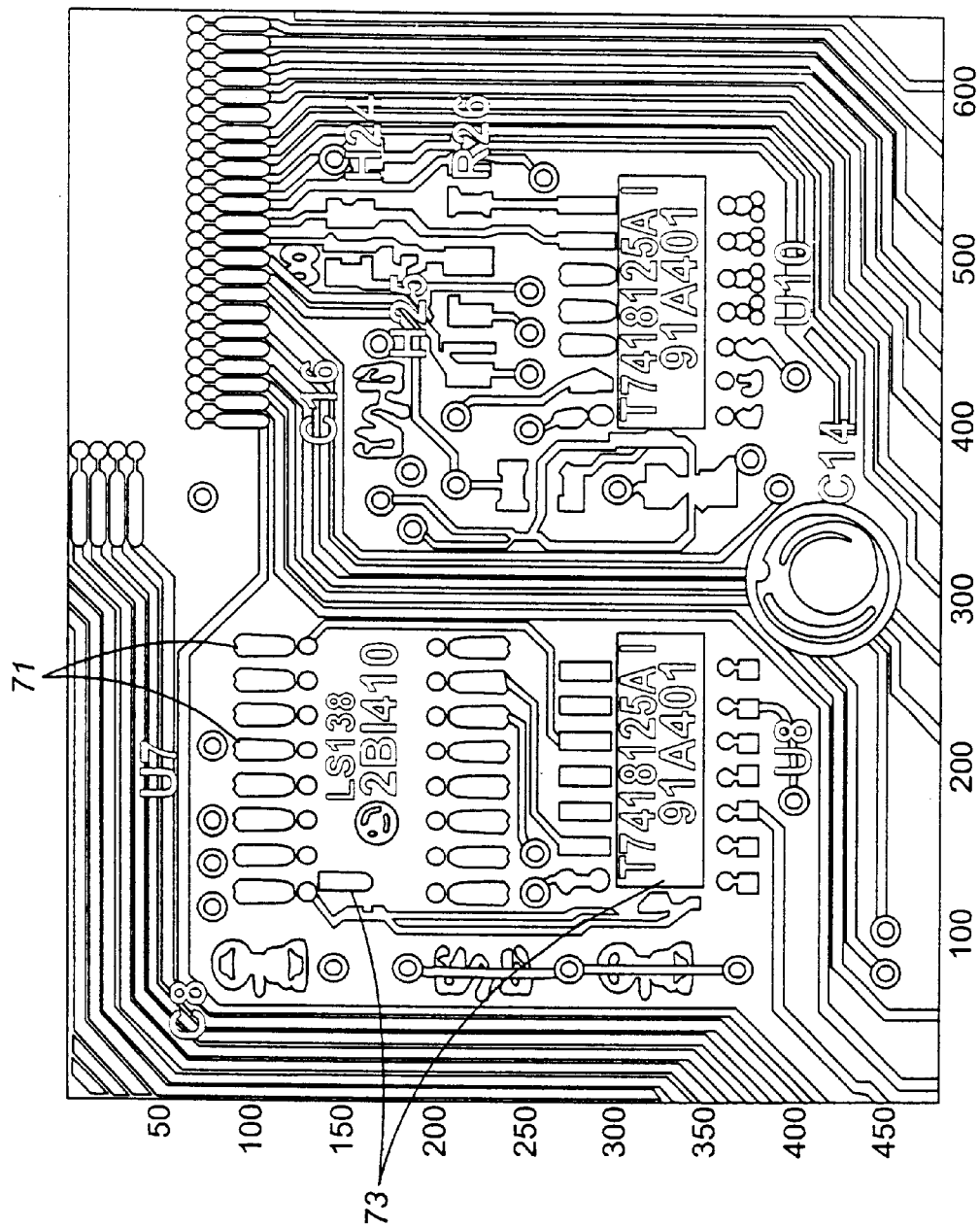
FIG. 8 illustrates a typical PCB image using diffuse front illumination

The shadow free images of a PCB are captured using flat illumination source. A red-pass filter is added to a light source to enhance the contrast of the green substrate and solder joints. FIG. 8 illustrates a typical surface mount component image.

Figure 9:
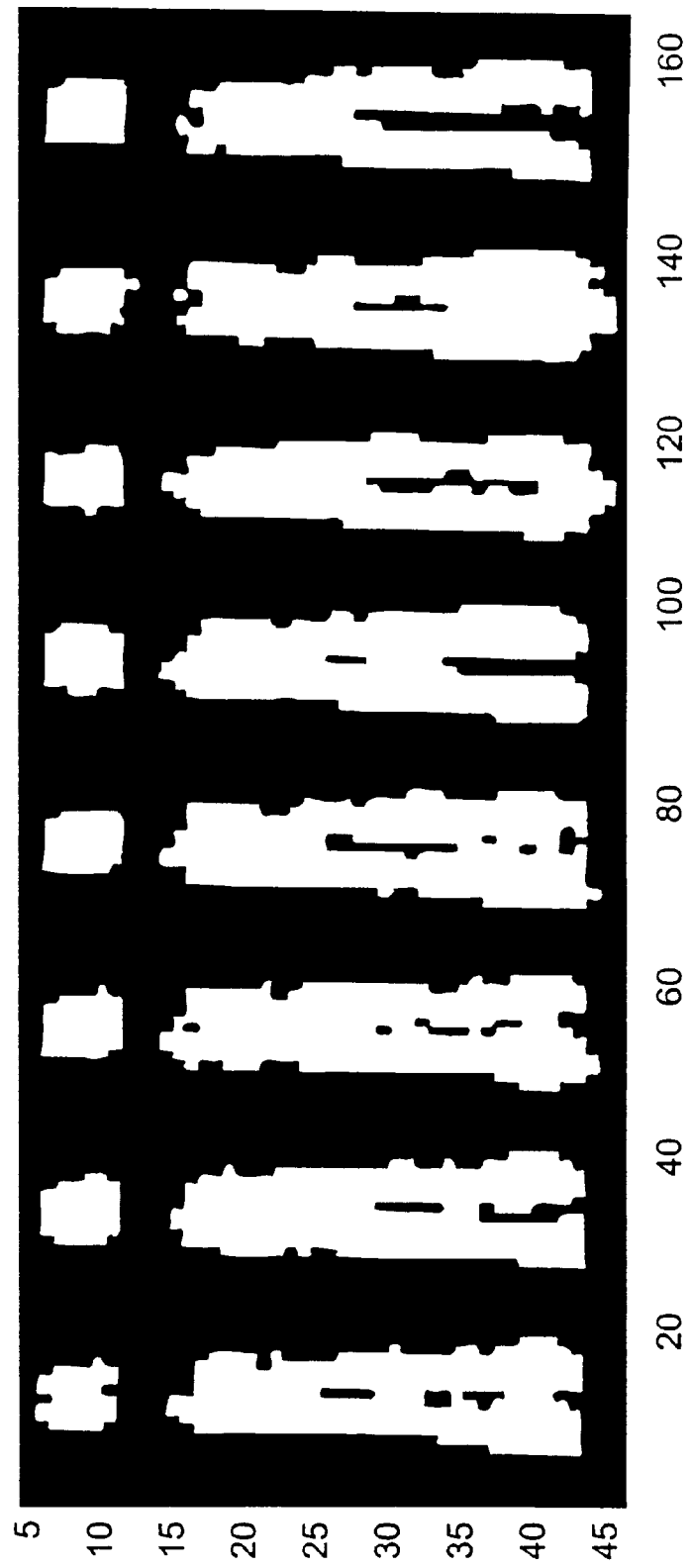
FIG. 9 illustrates a binary image of the leads of one side of an IC.

Programmed rectangular windows are used to get sub-images of the solder joints 71 of the components 73. From each sub-image a one-dimensional vector is obtained such that the information about component leads and their placement location on the solder pads is preserved. This vector is called a max scan. The peaks of the max scan represent solder joints and solder pads while valleys represent the substrate. To obtain a max scan from a sub-image, first the sub-image is segmented using a threshold. Since the histogram is bimodal, threshold selection is easy. FIG. 9 illustrates a binary image of one side of an integrated circuit's leads.

Consider an image I of size M×N, represented as pix(i,j), i=1, . . . , M, j=1, . . . ,N. pix(i,j) is the pixel value at location (i,j) in L Let S={$S_1, S_2, \ldots, S_j, \ldots, S_N$} be the max scan of I in the horizontal direction. The jth entry of S is calculated as $$s_j = \max_{k=1}^{M-Q+1} (a_{jk}), \quad (1)$$

where $a_{jk}$ is the average of the kth set of Q number of pixels in the JTH column of I. The $a_{jk}$ is calculated as $$a_{jk} = \frac{1}{Q} \sum_{i=0}^{Q-1} pix(k+i, j), \quad (2)$$

For a horizontal max scan, Equation 2 acts as a low pass filter in the vertical direction of the image I. By changing the value of Q, the filter cut-off frequency can be changed.

A max scan may have noisy peaks and valleys. To filter out such peaks and valleys, a morphological filter is applied to the max scan. The mathematical morphology is a tool for extracting two-dimensional image components that are useful in the description of the region shape such as boundaries, skeleton, and convex hull. It can also be used for pre- and post-processing, such as morphological filtering, thinning, and pruning. R. Gonzalez and R. Woods, *Digital Image Processing*, Addison-Wesley Publishing Company, Reading, Mass., 1992. The mathematical morphology can be applied to one-dimensional data also. Let $S_M$ be the output of the morphological filter, which is represented as, $$S_M = (((S \odot B) \oplus B) \oplus B) \odot B, \quad (3)$$

where B is the structuring element, "symbol bigdotO" is the erosion operation, and $\oplus$ is the dilation operation. For set X and Y in $Z^1$ one-dimensional space, the erosion of X by Y is defined as $$X \odot Y = \{I | (Y)_I \subseteq X\}, \quad (4)$$

which means that the erosion of X by Y is the set of all points x such that Y translated by x is contained in X. Mathematically, the translation of Y by x is defined as, $$(Y)_I = \{c | c = y + I, \text{ for } y \in Y\}. \quad (5)$$

The dilation of X by Y is defined as $$X \oplus Y = \{I | (\hat{Y})_I \cap X \neq \emptyset\} \quad (6)$$

which means that the dilation of X by Y is the set of all x translations of $\hat{Y}$, such that $\hat{Y}$, and X overlap by at least one nonzero element, where $\hat{Y}$ represents the reflection of Y, defined as $$\hat{Y} = \{c | c = -y, \text{ for } y \in Y\}. \quad (7)$$

Figure 10:
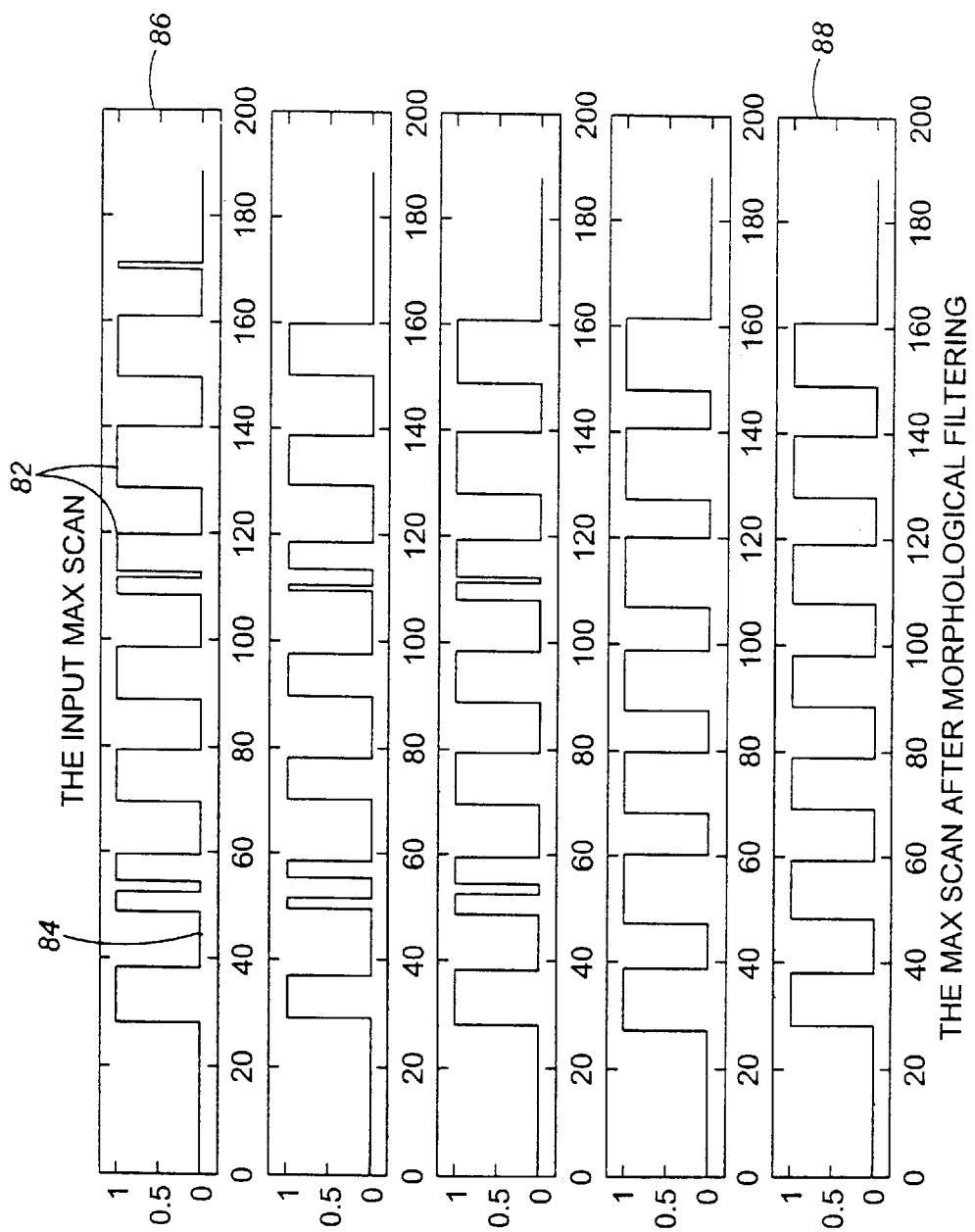
FIG. 10 illustrates the max scan at different stages of morphological filtering

Referring now to FIG. 10, the noisy peaks 82 and valleys 84 in the original max scan 86 are removed by the morphological filtering. After the morphological filtering, connectivity analysis is performed to determine the length of each bright and dark region encountered in the max scan 88. The member of peaks encountered gives information about the components' leads detected. The length of the bright region corresponds to the width of the solder joint and the length of a dark region corresponds to the distance between two adjacent solder joints. A fuzzy relation and linguistic variable based classifier, explained in the next section, has been developed to detect linear misalignment defects. A fuzzy classifier has been used to accommodate the uncertainty associated with the misalignment defect definition.

Angular Misalignment Test

Using the same segmented sub-image as used for the linear misalignment test, the outside corners of the first and last solder pad in the sub-image are determined using a search algorithm. Also the outside corner of the component's first and last lead on that side is determined. Let solder pads' corners be ($x_{p1}$, $y_{p1}$) and ($x_{p2}$, $y_{p2}$) A line $L_1$ passing through these points has the slope, $m_{pad}$, given as $$m_{pad} = \frac{y_{p2} - y_{p1}}{x_{p2} - x_{p1}} \quad (8)$$

Seymour Lipschutz, *Theory and Problems of Linear Algebra* 2nd Edition, McGraw-Hill, Inc. 1991, ch.1, pp.1–38.

Figure 11:
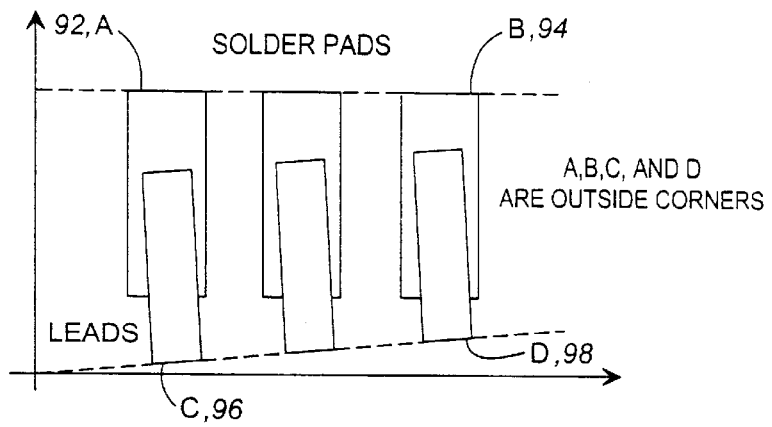
FIG. 11 shows an illustration of angular misalignment defect detection.

Similarly, the slope, $m_{lead}$, of the line passing through the outside corners of the component leads is determined. The difference of two slopes gives an error angle, calculated as follows:

$$\theta_{error} = |\tan^{-1}(m_{pad}) - \tan^{-1}(m_{lead})| \quad (9)$$

where | .| is an absolute operation. The $\theta_{error}$ is then compared with a predetermined threshold for the declaration of an angular misalignment defect. Referring to FIG. 11, an angular misalignment defect having A 92 and B 94 as the outside corners of solder pads and C 96 and D 98 as the outside corners of the component's leads.

Defect Identification using Fuzzy Relations and Linguistic Variables

To identify the defective solder joints at the GROSS inspection stage, a fuzzy classification approach using fuzz relations and linguistic variables is used. This classification scheme works on linguistic labels rather than numerical quantities and underlines a generality of the construction performed. Often pattern description is provided in a linguistic manner rather than precise numerical quantities. For example, a statement formulated by a human being with respect to recognition of a class ω would be, "If the object size is LARGE and its speed is FAST, then it belongs to class ω." The size and speed are linguistic variables taking values expressed as linguistic labels such as LARGE, SMALL, FAST, SLOW, etc. The linguistic labels can be modeled as fuzzy sets on an appropriate universe of discourse.

Let X be the object to be classified having features that take linguistic values such as zero, positive, negative, etc. If there are N such features, then there is a fuzzy relation $\Re$ on the universe $Z = U_1 \times U_2 \times \ldots \times U_n \times \ldots U_N$ where $U_n$ is the universe of discourse of the nth feature. Sankar K. Pal and D. Dutta Majumder, *Fuzzy Mathematical Approach to pattern Recognition*, John Wiley & Sons (Halsted), N.Y., 1986, ch. 3, pp 70–73. For fuzzy sets A, B on universe U, V, respectively, the membership of fit relation A×B on universe U×V is defined as $$\mu_{A \times B}(u,v) = \min\{\mu_A(u), \mu_B(v)\}, \forall u \in U, \forall v \in V \quad (10)$$

Lofti A. Zadeh, "Outline of a New Approach to the Analysis of Complex Systems and Decision processes", IEEE Transactions on Systems Man., Cybern., vol. SMC-3, no.1, pp.28–44, 1973.

where $\mu_A(u)$ is the membership of u in A and $\mu_B(v)$ is membership of v in B. Let the training set consist of L patterns partitioned into c classes, $\omega_k$, for k=1, . . . , c. Let $\Omega_j$, j=1, . . . ,L be a vector of size 1×c, representing the class membership of the jth pattern. The training patterns are expressed as fuzzy relations $u_j$, j=1, . . . ,L. By taking the Cartesian product of j, and $\Omega_j$,j=1, . . . , L, fuzzy relations are formed on the universe Z×[0,1]. The interval [0,1] represents the universe of discourse of $\Omega_j$. The relation, R, for the fuzzy classifier is obtained by, $$\mathcal{R} = \bigvee_{j=1}^{L} (\Upsilon_j \times \Omega_j) \quad (11)$$

where v is the symbol for the maximum operator. The quantity $Y_j \times \Omega_j$ is obtained using (10). Given an unknown pattern X with feature values, $\Phi_1(X), \Phi_2(X), \ldots, \Phi_N(X)$., its corresponding γ is obtained and then its class membership φ is calculated as, $$\gamma = \gamma \circ R \quad (12)$$

where o is the composition rule of inference. Lofti A. Zadeh, "Outline of a New Approach to the Analysis of Complex Systems and Decision processes", IEEE Transactions on Systems Man., Cybern., Vol. SMC-3, no.1, pp.28–44, 1973.

Figure 12:
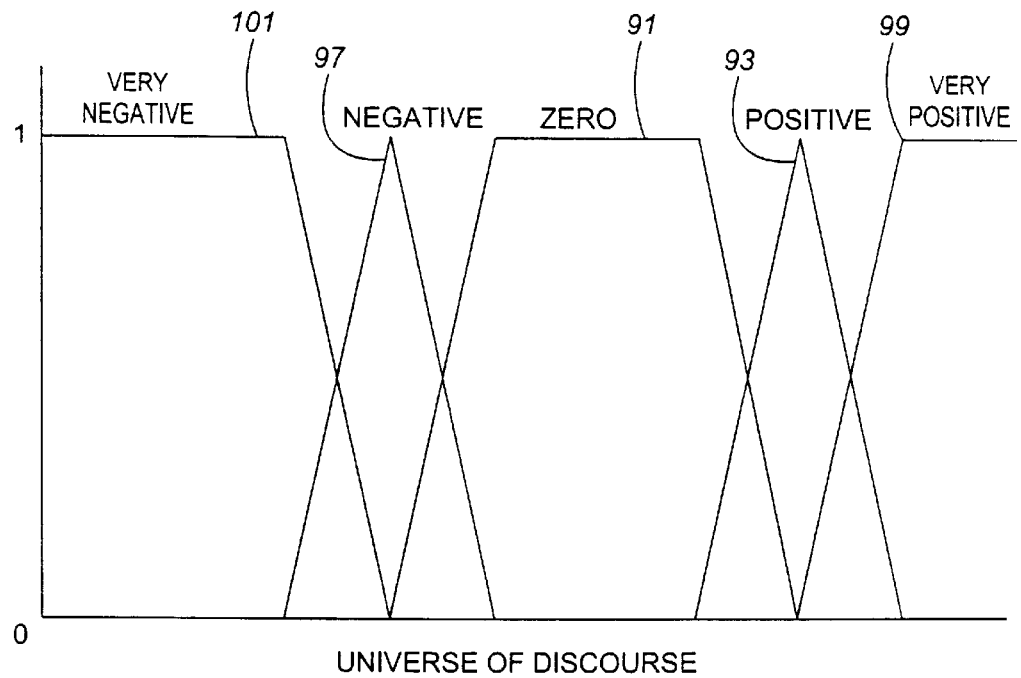
FIG. 12 illustrates the graphical representation of linguistic labels, ZERO, POSITIVE, NEGATIVE, VERY POSITIVE, and VERY NEGATIVE, as FUZZY sets.

Referring now to FIG. 12, let us consider the extracted features which are, solder joint width and the distance between two adjacent solder joints. Let the features be represented as a vector X={$x_1,x_2$} where $x_1$ is solder joint width and $x_2$ is the distance between the adjacent solder joints and the templates be represented as $T_k$={$t_{k1}, t_{k2}$}, k=1, . . . , p, where p is the surface mount components' type to be inspected. The templates are generated during the off-line training of the system. For the jth type surface mount component under inspection, an error vector E={$e_1,e_2$} is calculated where $e_1=x_1-t_{j1}$ and $e_2=x_2-t_{j2}$, which are the linguistic variables taking values expressed as linguistic labels ZERO 91, POSITIVE 93, NEGATIVE 97, VERY POSITIVE 99 and VERY NEGATIVE 101. FIG. 12 illustrates these linguistic labels represented as fuzz sets.

The fuzzy relations, γ, are constructed using the a priori information about specific good and defective solder joints. During the off-line training phase, the system generates the fuzzy relation $\mathcal{R}$ for the classifier. The training is completed in only one pass through the training data set.

IR Based GROSS Inspection

The purpose of the IR sensors in the GROSS inspection station is to detect subsurface and solder mass related defects. These defects include voids, insufficient, no solder, excess solder, solder ball, and bridging. These defects exhibit the gross characteristics of a significant variance in the amount of solder present on the component, since the IR signal is a function of the radiance of the component. I. Dar, K. Newman and G. Vachtsevanos, "Bond Validation of Surface Mount Components Using a Combined IR/Vision System", *Applied Machine Vision* 94 *Conference of SME*, Minneapolis, Minn., vol. 2, session 7, June 1994. The solder mass related defects can be divided into two general categories: excess solder mass, and insufficient solder mass. The excess solder mass category includes defects such as excess solder, solder ball, and bridging whereas the insufficient solder mass category includes defects such as voids, insufficient, and no solder. The IR based GROSS inspection identifies whether the solder joint under test is good or it belongs to one of two defect categories. Before explaining the details of IR based GROSS inspection algorithms, the emissivity dependence of a thermal signature, a limitation of IR based solder joint inspection, is discussed. A data-level sensor fusion methodology has been developed to obtain emissivity independent thermal signatures of solder joints.

Emissivity Dependent Thermal Signature

Figure 13:
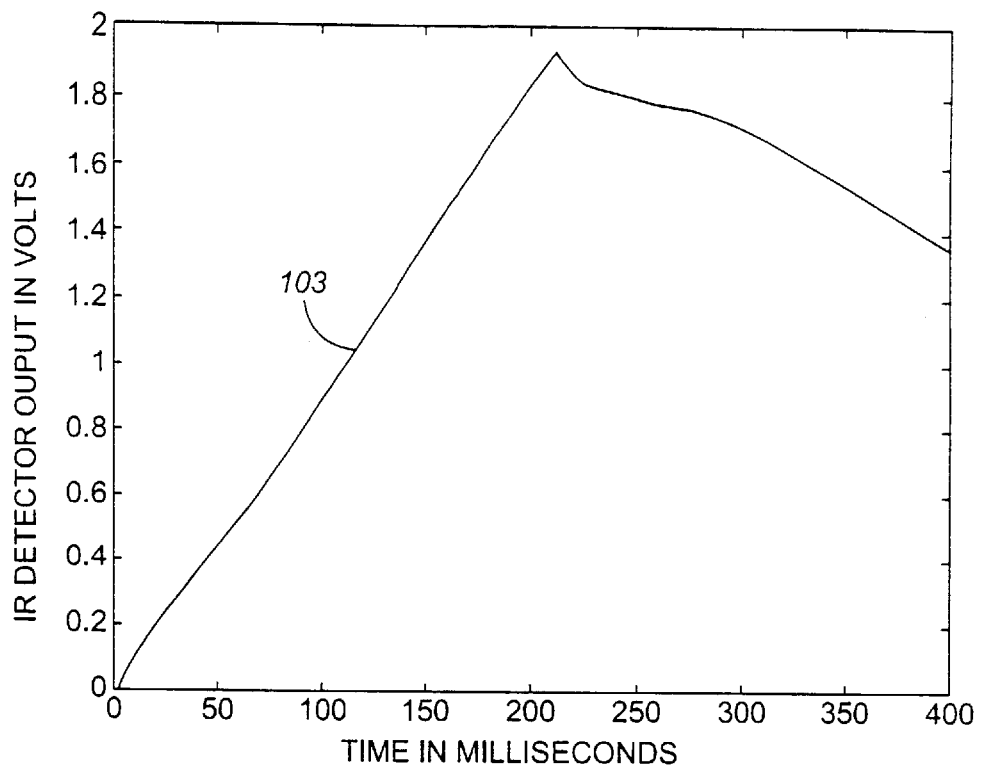
FIG. 13 illustrates a typical thermal signature of a solder joint.

Referring to FIG. 13, the IR technology utilizes IR thermal signatures of solder joints for inspection. These signatures are produced when a laser heats an individual solder joint and an IR sensor records its thermal radiation curve 103, called IR thermal signature or simply thermal signature. The thermal signature of a solder joint is a time series.

A problem associated with thermal signature analysis is that the sensor measurements are dependent on the emissivity of the solder joint. The IR radiant emittance, W, of a target is given as $$W = \epsilon \sigma T^4, \quad (13)$$

J. M. Lloyd, *Thermal imaging Systems*, Plenum Press, New York, 1975. where ε is the emissivity, T is temperature in degrees Kelvin, and a is the Stefan-Boltzmnann constant which is equal to $1.38054 \times 10^{-23}$. For an ideal blackbody, ε is equal to 1.0. The objects with radiation curves similar to those of a blackbody, but lower, are called graybodies. The ratio between the actual radiant emittance of an object and that of the blackbody value is the emissivity. Mathematically, $$\epsilon = \frac{W_{actual}}{W_{ideal}}. \quad (14)$$

The emissivity of unoxidized solder is between that of unoxidized tin (0.043) and unoxidized lead (0.05). CRC handbook of Chemistry & Physics, CRC Press Inc., Boca Raton, 49th edition, pp. E227. The emissivity of a solder joint can vary substantially because of differences in surface finish (i.e., a rough finish has higher emissivity because of greater absorption), the presence of pinholes, vents or blowholes, or surface contamination. The surface contamination may be present as genuine contamination or as normally occurring flux residues in a no-clean process. Varying emissivity changes the thermal signature of a joint in two ways. First, it increases the temperature rise of the joint because a higher emissivity surface absorbs more impinging radiation. Second, at a given temperature, the radiance is increased in direct proportion to the emissivity increase. These variations of emissivity add a random noise to the sensor measurement.

Fusion of IR Detectors

A sensor-fusion approach at data level has been developed to obtain emissivity-independent thermal signatures using two IR detectors sensitive in different radiation wavelengths. Planck's equation for the spectral distribution of a blackbody radiation provides a model of the radiance of a blackbody as a function of temperature and wavelength. It is given as $$W_\lambda = \frac{C_1}{\lambda^5 \left( \exp\left(\frac{C_2}{\lambda T}\right) - 1 \right)}, \quad (15)$$

Figure 14:
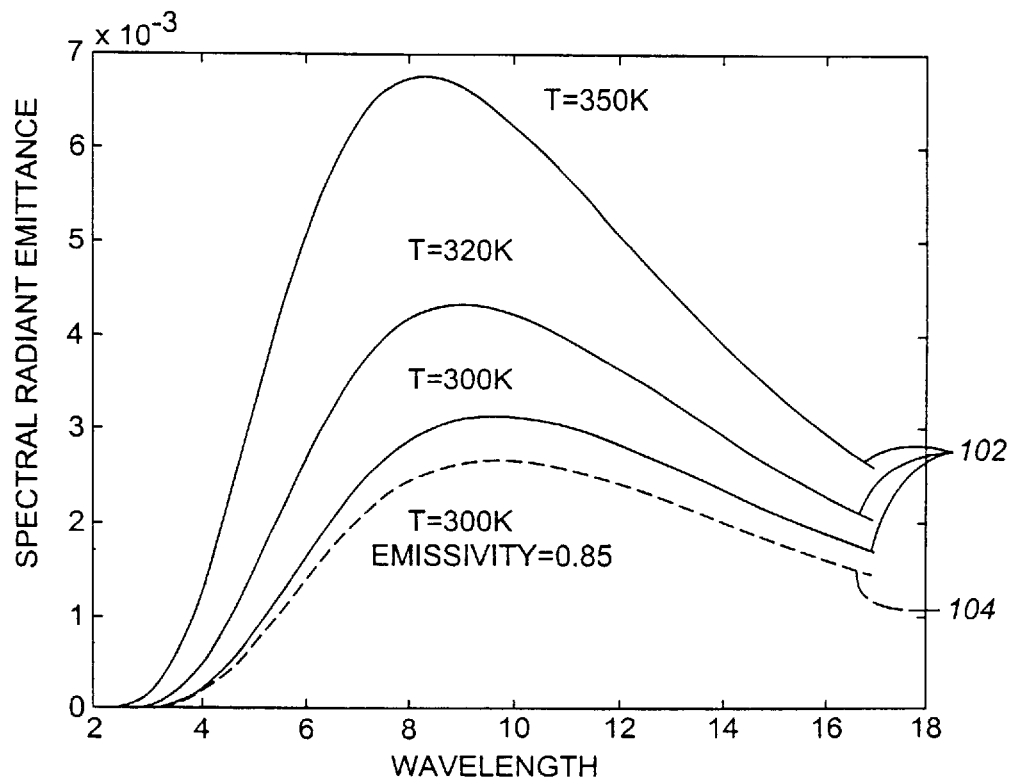
FIG. 14 illustrates spectral radiant emittance curves at different temperatures.

J. M. Lloyd, *Thermal imaging Systems*, Plenum Press, New York, 1975. where λ is the wavelength in μm, T is the temperature in degrees Kelvin, $C_1$ and $C_2$ are constants with values equal to $3.7415 \times 10^4$ and $1.4388 \times 10^4$, respectively. Referring to FIG. 14, three curves related to Equation 15 are depicted. The solid lines 102 show the spectral radiant emittance curves for a blackbody, while the dotted line 104 illustrates a spectral radiant emittance curve of a graybody with emissivity equal to 0.85.

The total radiance of a graybody at a given temperature is the area under its spectral radiant emittance at that temperature, i.e., the graybody spectral radiant emittance summed over all wavelengths at a given temperature. Mathematically, $$\mathcal{R} = \int_0^\infty \frac{\epsilon C_1}{\lambda^5 \left(\exp\left(\frac{C_2}{\lambda T}\right) - 1\right)} d\lambda. \tag{16}$$

Figure 15:
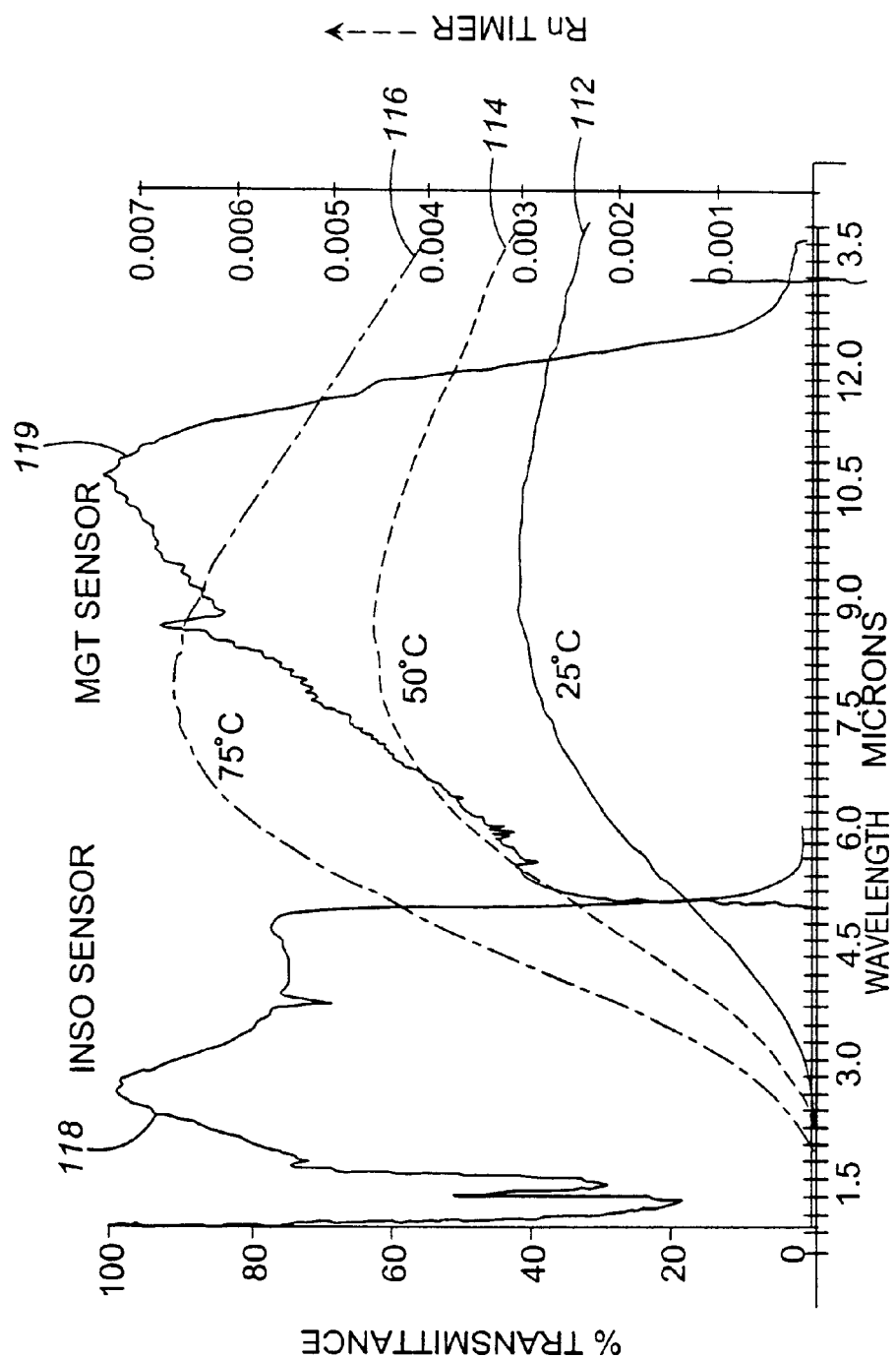
FIG. 15 illustrates blackbody spectral radiant emittance at different temperatures, superimposed on InSb and MCT detectors' sensitivity.

An IR detector functions by integrating the intensity of all wavelengths to which it is sensitive. For example, an Indium Antimonide (InSb) based IR detector is sensitive in the 2–5 μm range. Equation 16 for an InSb detector, can be written as $$\mathcal{R} = \underbrace{\int_1^5 \frac{\epsilon C_1}{\lambda^5 \left(\exp\left(\frac{C_2}{\lambda T}\right) - 1\right)} d\lambda}_{v} + \mathcal{N}, \tag{17}$$

where N represents radiance outside the sensitive band of the detector, v is the output voltage of the sensor that represents the IR energy in the detector's sensitive band. Due consideration should be given to the information being lost because of the IR detector bandwidth limitations. The MCT detector is sensitive in the 6–12 μm range. Referring now to FIG. 15, the blackbody spectral radiant emittance curves for 25° C. 112, 50° C. 114, and 75° C. 116 are superimposed on the sensitivity curves of an InSb detector 118 and a Mercury-Cadmium-Telluride (MCT) detector 119. FIG. 15 illustrates that a large portion of the radiance curves lies within the two detectors' sensitive range. Since solder joints are heated to 75° C. or less for inspection purposes, it is more appropriate to use both the IR detectors to measure the thermal signature of solder joints. For the two IR detector cases, Equation 16 becomes $$\mathcal{R} = \underbrace{\int_1^5 \frac{\epsilon C_1}{\lambda^5 \left(\exp\left(\frac{C_2}{\lambda T}\right) - 1\right)} d\lambda}_{v_1} + \underbrace{\int_6^{12} \frac{\epsilon C_1}{\lambda^5 \left(\exp\left(\frac{C_2}{\lambda T}\right) - 1\right)} d\lambda}_{v_2} + \mathcal{N}, \tag{18}$$

where $v_1$ represents the output voltage of InSb detector and $v_2$ represents the output voltage of MCT detector. Notice that in Equation 18 $\epsilon$ is a constant with respect to the integral. The IR detectors' output is fused by taking the ratio of the detectors' output. Let Z be the ratio of the MCT detector's output and the InSb detector's output. Mathematically, $$Z = \frac{\epsilon \int_6^{12} \frac{C_1}{\lambda^5 \left(\exp\left(\frac{C_2}{\lambda T}\right) - 1\right)} d\lambda}{\epsilon \int_1^5 \frac{C_1}{\lambda^5 \left(\exp\left(\frac{C_2}{\lambda T}\right) - 1\right)} d\lambda}. \tag{19}$$

In Equation 19, $\epsilon$ cancels out, therefore Z is independent of the emissivity. Equation 19 can be written in terms of the detectors' voltage as $$Z = \frac{v_2}{v_1}. \tag{20}$$

Figure 16:
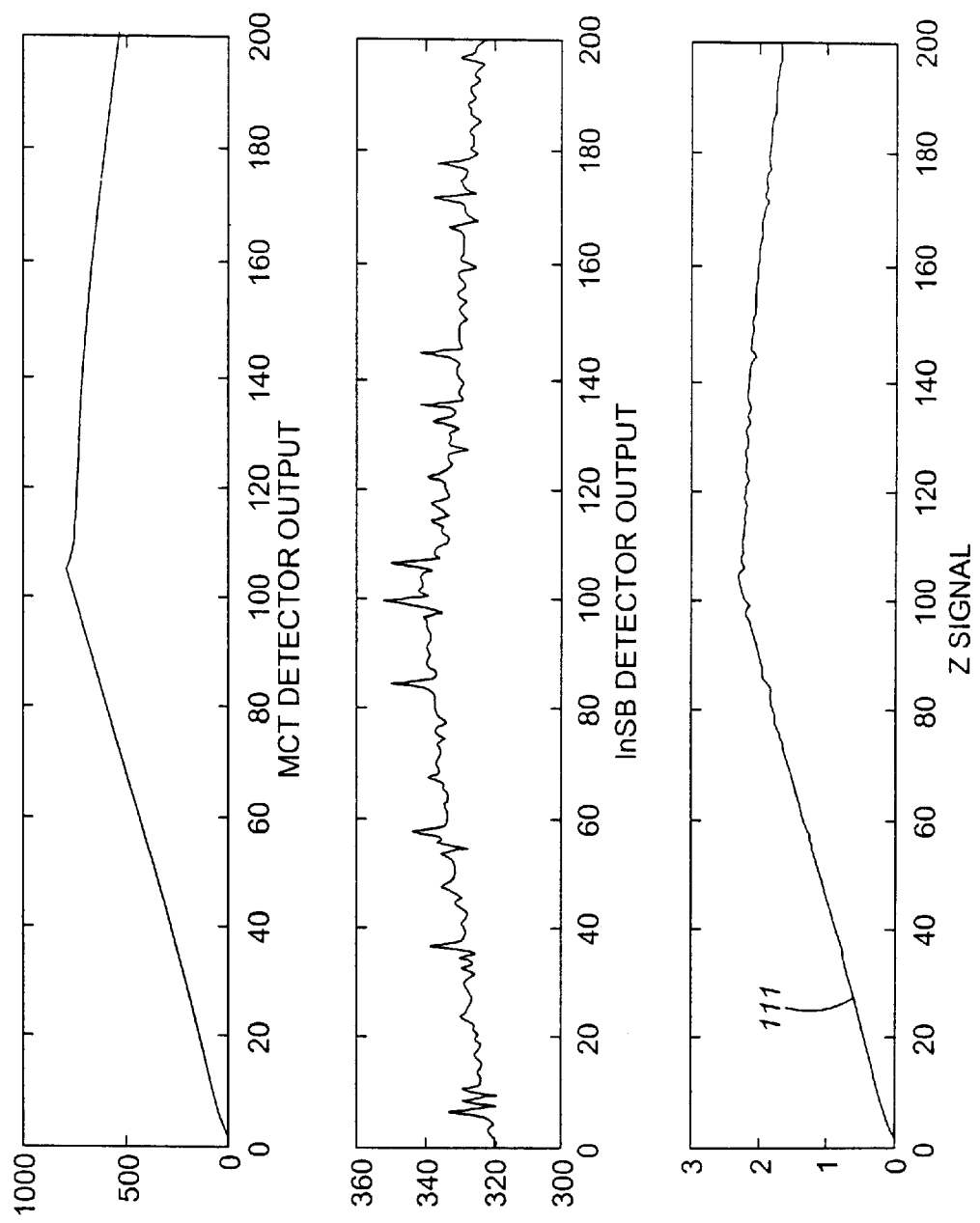
FIG. 16 illustrates the Z signal.

FIG. 16 illustrates the Z signal 111 obtained by fusing the outputs of the MCT and InSb IR detectors.

GROSS Inspection using Thermal Signatures

Figure 17:
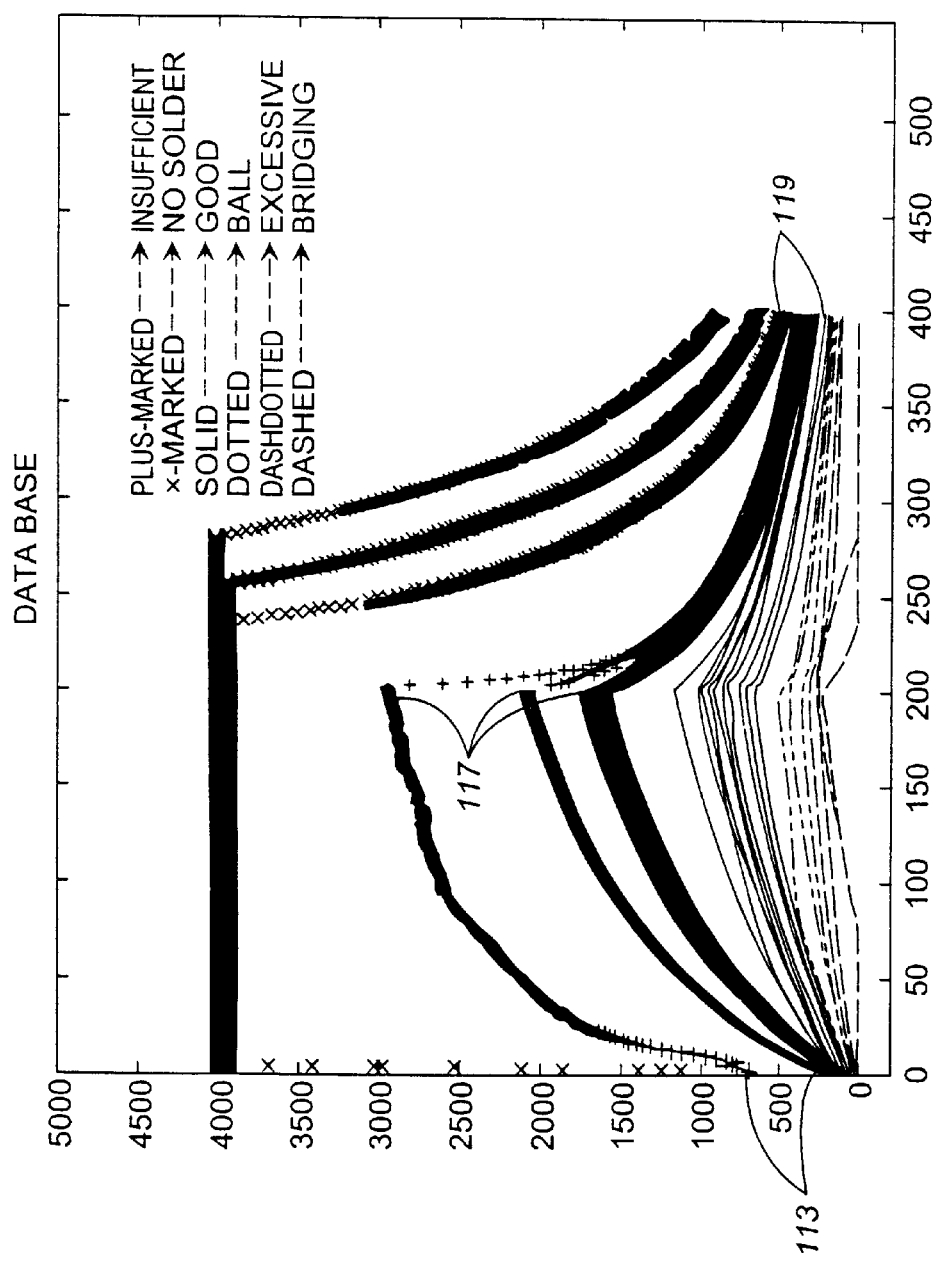
FIG. 17 illustrates the Z signals of good and defective solder joints.

To identify solder joint defects using thermal signature, features are determined that maximize the variation between the good solder joint signature and the defective solder joint signature. In the insufficient solder mass category, there is a lack of solder; therefore, for the same laser heating time, the signature will be elevated because of an increase in IR radiation. For the excess solder mass category, there is an excess of solder, thereby decreasing the amount of the IR radiated from the joint and lowering the thermal signature. FIG. 17 illustrates the Z signals of solder joints of an integrated circuit.

The number of joints to be tested is determined prior to inspection by a random sampling scheme. This is a function of the perceptance of inspection to be performed. The amount of time required for the inspection of one joint is approximately 500 milliseconds. This takes into consideration the amount of time required to position the joint using X-Y table, fire the laser, collect the data, and process the information. The majority of the time is devoted to the collection of the signature which takes on average 400 milliseconds. Inspection of a largely populated board would be time consuming if 100% inspection was desired. This is the reason for the sampling methodology for on-line applications.

Figure 18:
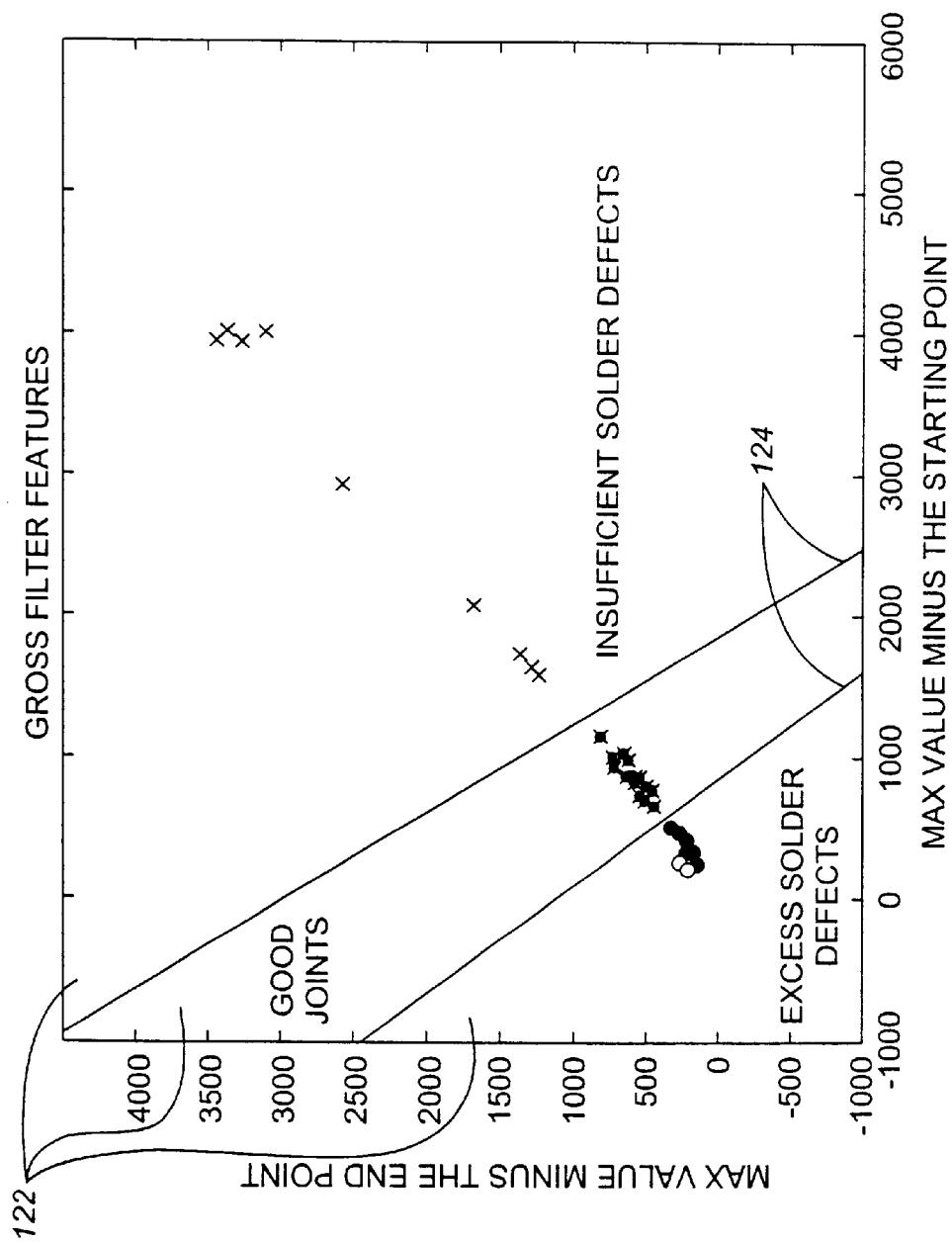
FIG. 18 illustrates the feature space for IR based GROSS inspection.

The two most noticeable and easy to obtain features in the Z signals are the differences between the starting point 113 and the maximum point 117, and the maximum point 117 and the end point 119. These features can be determined rapidly from the data. Referring to FIG. 18, the feature space 122 and the decision boundaries 124 for the GROSS inspection are shown. Since the feature space is linearly separable, a perceptron classifier has been designed to perform the classification.

FINE Inspection Software

The potentially defective solder joints, identified by the GROSS inspection, are analyzed more closely in order to confirm the joints' defects and classify them into defect categories. This classification is performed using information provided by the two-dimensional gray level images of the solder joints and their thermal signatures. The software developed for the FINE inspection station performs sensor fusion at feature level using an active perception approach. The active perception methodology developed for the FINE inspection not only fuses the complementary information obtained from the IR sensors and vision sensors but also minimizes the processing time by controlling the information gathering process. The premise used for this control is to acquire only that much information which is required to perform the task at hand. The active perception approach is generic in the sense that it can be applied to a multi sensor environment as well as to the features extracted from a single sensor.

Figure 19:
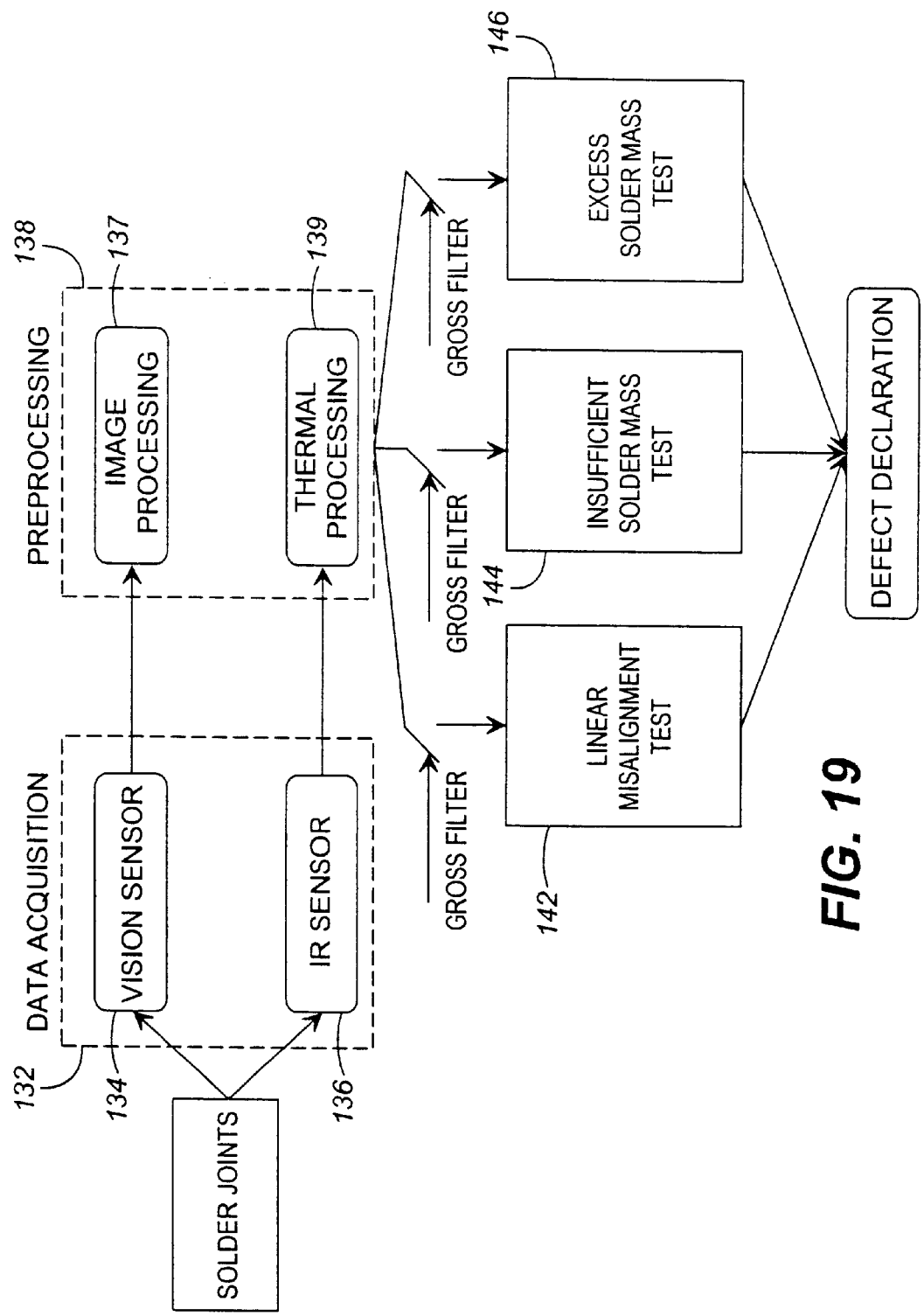
FIG. 19 illustrates the block diagram of PINE inspection procedure.
Figure 20:
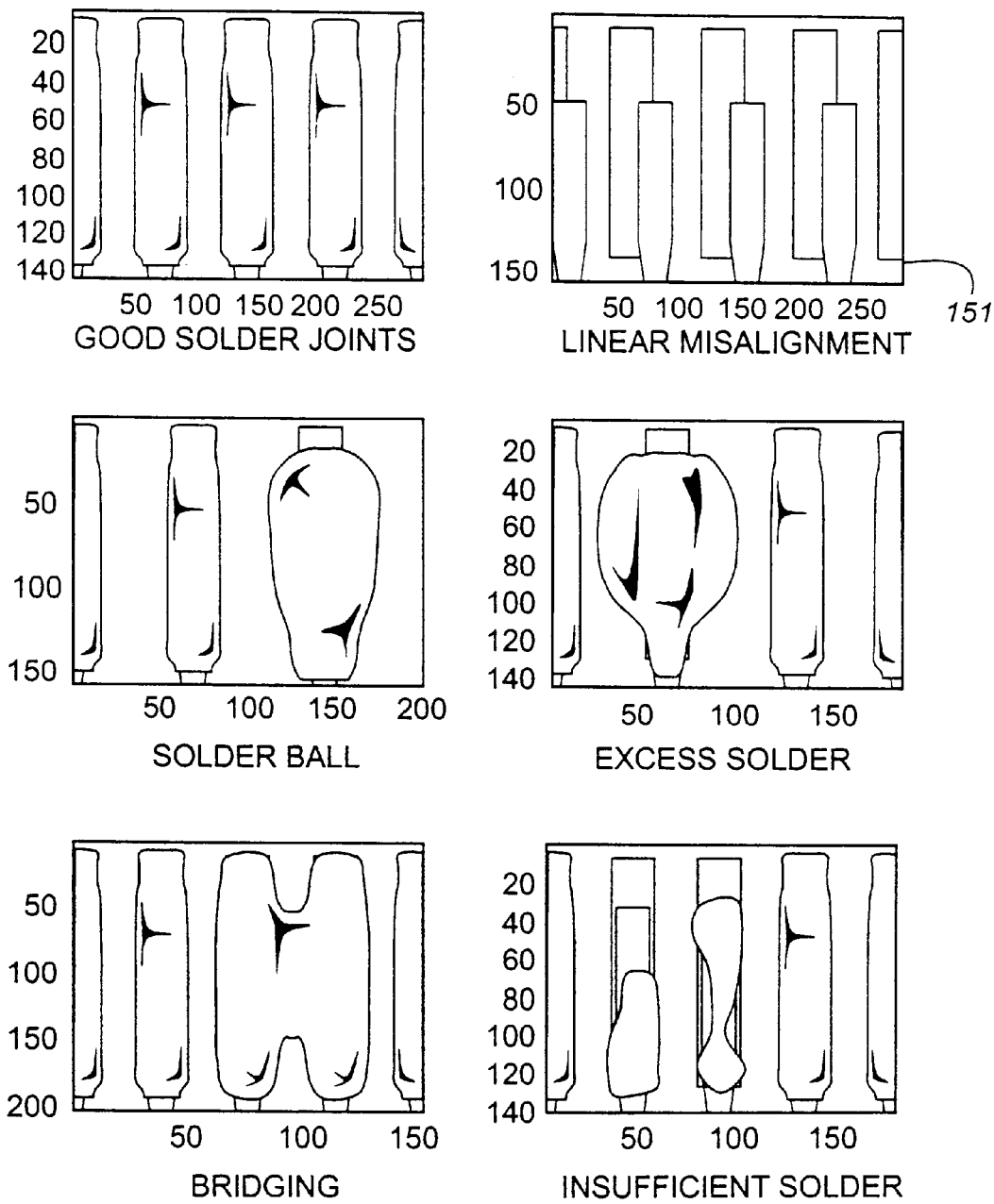
FIG. 20 illustrates good solder joints and typical solder joints defects.

FIG. 19 illustrates the block diagram of the FINE inspection procedure. The data acquisition module 132 consists of a vision sensor 134 and a two color IR sensor 136. The vision sensor provides high resolution two-dimensional images of the solder joints while the two color IR sensor generates thermal signatures of the joints. FIG. 20 illustrates an image of good solder joints and typical images of some of the solder joint defect categories.

The IR sensor data is fused at the data level to obtain a Z signal, as explained in the previous section titled IR Based GROSS Inspection. A pre-processing module 138 includes an image processing means 137 for converting the images captured by the vision system, and a thermal processing means 139 for converting the thermal signatures recorded by the infrared sensors into a form from which characteristic features of different defect classes can be easily extracted. The pre-processing involves operations such as frequency domain filtering, spatial filtering and enhancement by noise removal. Since the FINE inspection is performed only if GROSS inspection detects a potential linear misalignment defect, excess solder mass defect, and/or insufficient solder mass defect, the FINE inspection procedure is broken down into three modules. These modules are linear misalignment test 142, insufficient solder mass test 144, and excess solder mass test 146. The linear misalignment test 142 confirms whether the potentially defective joints are linearly misaligned. The insufficient solder mass test 144 classifies a potential defective joint into good, void, insufficient solder, or no solder categories. The excess solder mass test 146 classifies a potential defective joint into good, bridging, excess solder, or solder ball categories. The excess solder mass test 146 and the insufficient solder mass test 144 modules use the active perception methodology to perform feature-level sensor fusion for defect classification. Before presenting the details of each of these modules, the active perception for feature-level sensor fusion is explained.

Active Perception

Active perception can be defined as the problem of controlling one or more sensors during data acquisition to maximize the performance of the information-gathering process. Human perception is primarily governed by this concept. If we analyze the human perception process, it appears that perception involves adaptiveness and intelligence to reason and make decisions as quickly as possible. These attributes are desirable for machine perception as well, which usually involves processing a large number of data sets originating from one or more sensors.

The objective of active perception is to achieve reliable recognition in a minimum amount of time. The conventional machine perception or pattern recognition approach involves a sequence of steps, namely, data acquisition, feature extraction/selection, and classification. The feature extraction process converts the objects into an N-dimensional feature space, such that one class of objects is clustered together and can be distinguished from other classes. However, in general, not all objects of a class need N features to form a compact cluster. It is only the objects that are in the overlapping region of two or more classes that govern the number of features required to perform classification. If there is a way to judge the classifier result at each feature, then one could optimize the perception procedure by using that much information, which is sufficient for the task at hand. An index has been derived using the Dempster Shafer theory and fuzz logic, which represents the faith or confidence committed to a classification result. This index is called degree of certainty (DOC).

Degree of Certainty

For a frame of discernment $\theta$ and a proposition $A \subset \theta$, the degree of certainty associated with A, DOC(A), is defined as $$DOC(A)=m(A)-Bel(\overline{A}), \qquad (21)$$

where m (.) represents the mass function, Bel (.) represents the belief function over $\theta$ and $\overline{A}$ represents the complement of A.

The belief function over $\theta$ is defined by Bel: $2^\theta [0,1]$ and derived from the mass function m by $$Bel(A) = \sum_{B \subset A} m(B) \quad \forall A \subseteq \theta. \qquad (22)$$

G. Shafer, *A Mathematical Theory of Evidence*, Princeton University Press, New Jersey, 1976.

The value of DOC indicates a relative amount of belief or confidence in the frame of discernment. The properties of DOC with appropriate explanations are given below.

DOC has a value in [−1,1].

DOC(A)=1 indicates that the evidence supports A exclusively because m(A)=1 is always satisfied.

DOC(A)=0 is satisfied when m(A)=m($\overline{A}$), which implies that the amount of belief on A is equal to that of belief on the rest of $\theta$.

DOC(A)=−1 indicates that Pl(A)=1−Bel(A)=0, which implies that evidence does not support A at all.

From equation 21 it is clear that in order to calculate DOC associated with any one or more atomic propositions, the mass function needs to be determined first. Once the mass function for all the subsets of $2^\theta$ has been calculated, the belief function can be estimated for any subset of $\theta$ by using Equation 22. Finally, the DOC for any subset of $2^\theta$ can be calculated using Equation 21.

Calculation of Mass Function

In this section, a systematic approach is derived using fuzzy logic and possibility measure to calculate mass function on a frame of discernment. A family of subsets of a universal set is nested if these subsets can be ordered in such a way that each is contained within the next. Consider a body of evidence whose focal elements are nested. For such a body of evidence, the associated belief and plausibility measures are called consonant. G. J. Klir and T. A. Folger, Fuzzy Sets, Uncertainty, and Information, Prentice-Hall Inc., Englewood Cliffs, N.J., 1991. Consonant belief and plausibility measures are usually referred to as necessity measure and possibility measure, respectively. Let $F=\{x_1, x_2, \ldots x_n\}$ be a body of evidence with n nested focal elements such that $F=\{A_i | A_1 \subset A_2 \ldots \subset A_n\}$, where $A_i \in 2^F$. If $\pi$ and $\eta$ denote a possibility measure and a necessity measure on $2^F$, respectively, then $$\eta(A \cap B)=\min [\eta(A), \eta(B)] \; \forall A, B \in 2^F \qquad (23)$$

and $$\pi(A \cap B)=\max [\pi(A), \pi(B)] \; \forall A, B \in 2^F \qquad (24)$$

Every possibility measure $\pi$ defined on $2^F$ can be uniquely determined by a possibility distribution function pd: F→[0, 1], as $$\pi(A) = \max_{x \in A} pd(x) \quad \forall A \in 2^F. \tag{25}$$

G. J. Klir and T. A. Folger, *Fuzzy Sets, Uncertainty, and Information*, Prentice-Hall Inc., Englewood Cliffs, N.J., 1991.

Figure 21:
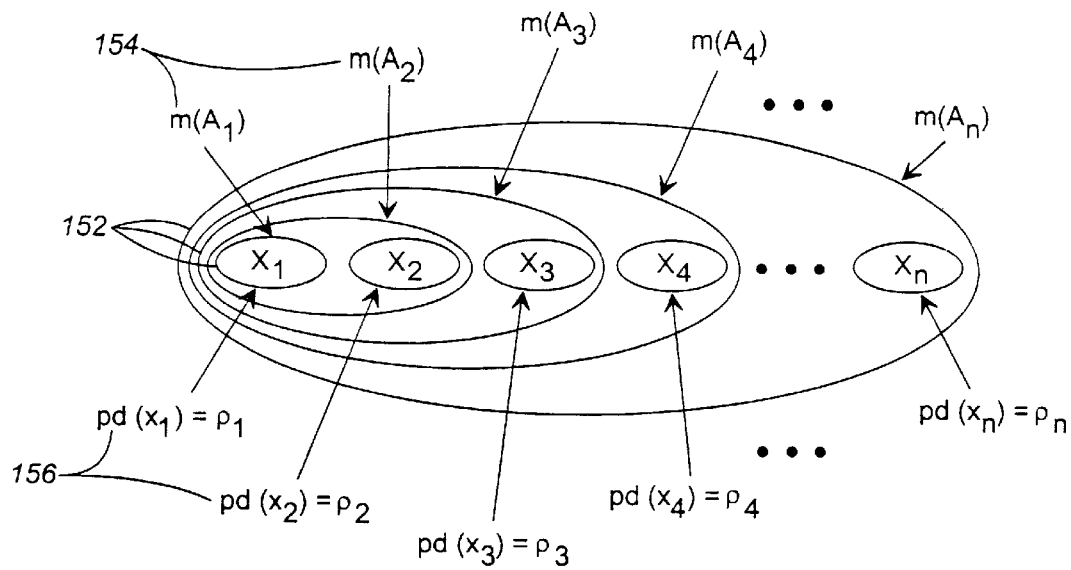
FIG. 21 illustrates a sequence of nested subsets of $\Theta$.

Let a possibility distribution function pd be defined on a frame of discernment $\theta = \{x_1, x_2, \ldots x_n\}$ with nested focal elements. A possibility distribution associated with pd is given as $$pd = (\rho_1, \rho_2, \ldots, \rho_n), \tag{26}$$

where $\rho_1 = pd(x_i)$ for all $x_i \in \theta$. Assume that a possibility measure $\pi$ is defined on $2^\theta$ in terms of its mass function m. FIG. 21 illustrates a complete sequence of nested subsets of $\theta$ 152 with associated mass function 154 and possibility distribution function 156.

From the definition of possibility measure as consonant plausibility measure and using Equation 24 and Equation 25 it follows that $$\rho_i = pd(x_i) = \pi(\{x_i\}) = Pl(\{x_i\})$$

for all $x \in \theta$. The relationship between possibility measure and mass function is given as $$Pl(A) = \sum_{A \cap B \neq \emptyset} m(B) \quad \forall A \subseteq \theta, \tag{27}$$

G. Shafer, A Mathematical Theory of Evidence, Princeton University Press, N.J. 1976.
where $\theta$ is the null set. Thus, it can be obtained from Equation 27

$$\rho_i = Pl(\{x_i\}) = \sum_{k=i}^{n} m(A_k) \tag{28}$$

since $x_i \in A_j \ \forall j \leq i$, a condition satisfied because of nested focal elements of $\theta$. Equation 28 can be written as a set of equations for $i = \{1, 2, \ldots, n\}$. These equations are $$\begin{aligned}
\rho_1 &= m(A_1) + m(A_2) + \cdots + m(A_i) + \cdots + m(A_n) \\
\rho_2 &= m(A_2) + \cdots + m(A_i) + \cdots + m(A_n) \\
&\vdots \\
\rho_i &= m(A_i) + \cdots + m(A_n) \\
&\vdots \\
\rho_n &= m(A_n).
\end{aligned}$$

Solving these equations for $A_i$, $i = \{1, 2, \ldots, n\}$, the relation between possibility measure and mass function is obtained as $$m(A_i) = \pi(\{I_i\}) - \pi(\{I_{i+1}\}) \quad \forall \text{ integer } i, \tag{29}$$

where $\pi(\{x_{n+1}\}) = 0$.

Figure 22:
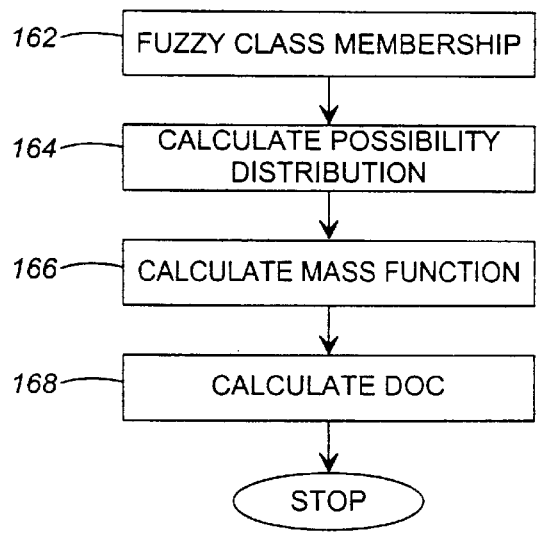
FIG. 22 illustrates the flow chart of DOC calculation procedure.

Zadeh founded the fry set theory in which a fuzzy set is viewed as a basis for possibility theory. L. Zadeh, "*Fuzzy sets as a basis for a theory of possibility*", Fuzzy Sets and Systems, vol. 1, pp.3–28, 1978. Let Z be a fuzzy set of a universe of discourse U, which is characterized by the membership function $\mu$, with the grade of membership, $\mu_z(u)$ $\forall u \in U$. Let X be a variable taking values in U, and let Z act as a fuzz restriction, R(X, associated with X. Then, the proposition "X is Z," which can be written as R()=Z, associates a possibility distribution, $\pi_x$ with X, which is postulated to be equal to R(X), i.e., $\pi_x = R(X)$. The possibility distribution function, $pd_x$, associated with $\pi_x$ is defined to be equal to the membership function of Z. Thus, $pd_x(u)$, the possibility that X=u is postulated to be equal to $\mu_z(u)$. Referring to FIG. 22, the steps required for DOC calculation for a pattern recognition approach are illustrated and can be summarized as follows:

Obtain a fuzzy set representing the membership 162 of the unknown pattern to all the possible classes. Rearrange the fuzzy set in descending order such that the first entry of the set represents the class with maximum membership. To obtain a possibility distribution 164, normalize the fuzzy set with respect to the maximum membership so that the maximum becomes equal to one. The mass function 166 for a nested body of evidence is calculated via Equation 29.

DOC 168 associated with each class is then calculated via Equation 21.

Active Perception in Sensor Fusion

In this section the active perception approach which performs the sensor fusion at feature level is explained. Let $F = \{F_1, \ldots F_n\}$ be a set of n features extracted from the data obtained from m sensors to perform classification over the frame of discernment $\theta$ having c atomic propositions. A total of n evidence can be generated using the n available features. Each evidence is represented as set of mass functions calculated from the fuzzy classifier output using the procedure explained in the section titled "Calculation of Mass Function". The evidence $E_i$ is generated based on the ith feature by performing fuzzy classification using $F_i$, only. The evidence $E_i$ obtained from the ith feature and evidence $E_j$ obtained from the jth feature are combined using Dempster's rule of combination. For two body of evidence, represented as mass functions $m_1$ and $m_2$, the combined body of evidence, $m_{1,2}$, is obtained using the Dempster's rule of combination as $$m_{1,2}(A) = \frac{\sum_{B_i \cap C_j = A} m_1(B_i) m_2(C_j)}{1 - K} \quad \forall A \in \theta, A \neq \emptyset, \tag{30}$$

G. Shafer, A Mathematical Theory of Evidence, Princeton University Press, New Jersey, 1976.
where K is calculated by, $$K = \sum_{B_i \cap C_j = \emptyset} m_1(B_i) m_2(C_j). \tag{31}$$

For active perception, $F_i$, and $F_j$, could be obtained from a single sensor data or from multiple sensor data to provide a combined body of evidence. Once a combined body of evidence is obtained, DOC associated with any subset of $2^\theta$ can be calculated using Equation 21.

Figure 23:
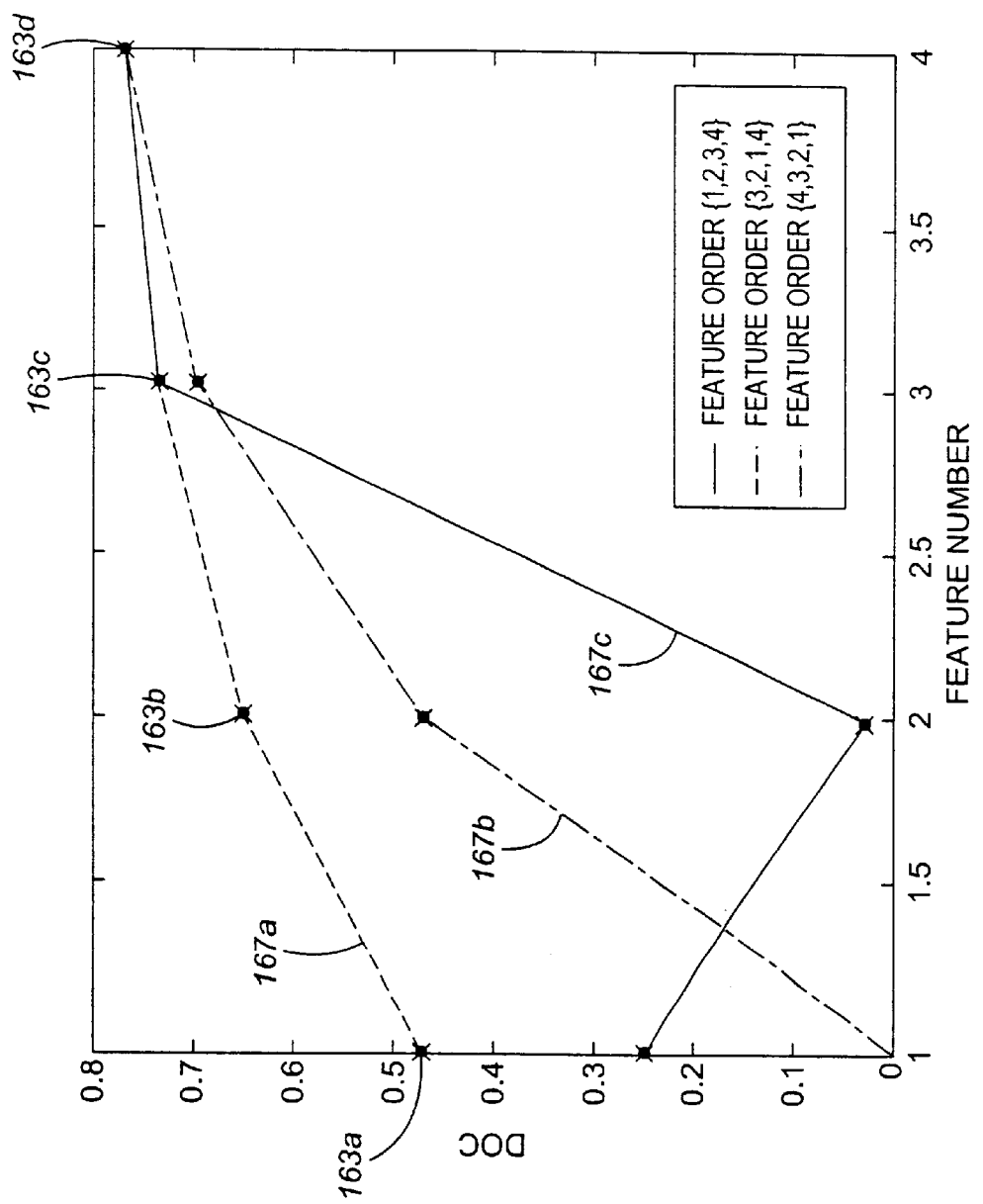
FIG. 23 illustrates DOC trajectories for class A.

The body of evidence $E_{1, \ldots, n}$, obtained by pooling n evidence is independent of the order in which pooling is performed. Therefore, the DOC associated with $E_{1, \ldots, n}$ is also independent of the evidence pooling order. However, the DOC trajectories are dependent on the order in which the pooling of evidence is performed. The DOC trajectories represent a set of loci on a two-dimensional plane whose axes are DOC and feature number. Let all the available features be ordered in a sequence. The DOC trajectory for the kth ordered feature $F_k$ can be written as $$\vec{t}(k) = k\vec{f} + a_k\vec{D}, \tag{32}$$

where f (with overhead vector arrow) and D (with overhead vector arrow) are unit vectors in the feature number and DOC axis, respectively. The sum of t (with overhead vector arrow) (k)+t (with overhead vector arrow) (k+1) is obtained as $$\vec{t}(k+\vec{t}(k+1) = (k+1)\vec{f} + (a_k \Re a_{k+a})\vec{D}, \tag{32}$$

where $\Re$ represents Dempster's rule of combination. Since, in general, $a_i \Re a_j \neq a_j \Re a_q$ for $j \neq q$, it is clear that the DOC trajectory is dependent on the order in which the various pieces of evidence are combined. Because evidence is obtained from the features, this implies that DOC is dependent on the feature ordering. FIG. 23 illustrates an example of DOC trajectories when four pieces of evidence 163a, 163b, 163c and 163d are combined in three different orders 167a, 167b and 167c. The four evidence expressed as mass functions are given in Table A

| Evidence | Mass Functions |
|---|---|
| $\epsilon_1$ | $m_1(A) = 0.250$  $m_1(ABC) = 0.750$ |
| $\epsilon_2$ | $m_2(C) = 0.222$  $m_y(AC) = 0.333$  $m_y(ABC) = 0.444$ |
| $\epsilon_3$ | $m_3(A) = 0.474$  $m_z(AB) = 0.474$  $m_z(ABC) = 0.052$ |
| $\epsilon_4$ | $m_4(AB) = 1.000$ |

Figure 24:
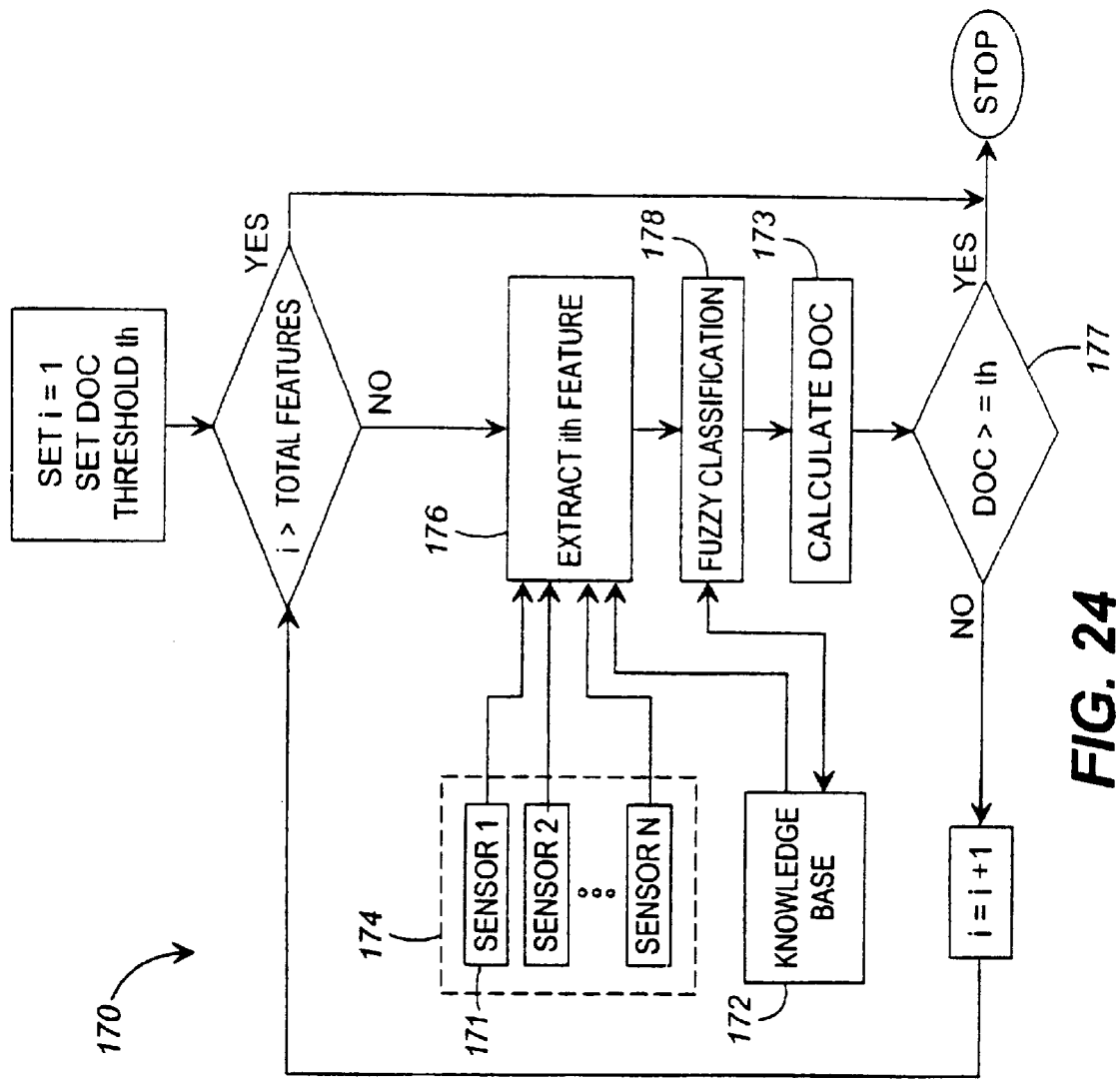
FIG. 24 illustrates the active perception procedure for defect classification.

For supervised classification approaches, the a priori information about the classes is available in the form of a training data set. Using the training data set, the distinguishability power of each feature can be determined. Thus, it is a reasonable assumption that the knowledge base contains information about the distinguishability of features of each object as well as the time necessary to measure the features. It is generally true that the time required to derive a set of mass functions differs widely from one feature class to another, as much as from one sensor to another similar device. In order to achieve a reliable classification in the minimum amount of time, the features should be aligned in an optimal order such that features that require less processing time and provide greater distinguishability between classes should be first in the feature-ordering scheme. Assuming that an ordered feature set has been obtained, fuzzy classification is performed using one feature at a time from the ordered feature set. Each classification result based on a feature is converted into a body of evidence. Thus, for each feature, the classifier provides a piece of evidence. To determine the degree of perception achieved based on the latest evidence and all the previous evidence, DOC associated with the combined body of evidence is calculated. The total evidence is aggregated until the required DOC is achieved. The process of fuzzy classification is stopped as soon as enough evidence is obtained to achieve a pre-specified DOC. Thus, the active perception scheme controls the information-gathering process and uses that much information that is sufficient for the task at hand. FIG. 24 illustrates the active perception approach for a multisensory environment.

Referring to FIG. 24, the active perception procedure 170 for defect classification is shown. The knowledge base 172, represents the database including the optimal feature ordering and the training data set for the f classifier. The active perception procedure is generic in the sense that it can be applied in a multisensory 174 environment to perform sensor fusion at the feature level or on only the features extracted from a single sensor 171. Features are extracted 176 and a fuzzy classification 178 is performed. A DOC is calculated 173 and a decision 177 is made on whether DOC threshold has been reached. If DOC threshold has not been reached an additional feature is considered. Once DOC threshold has been reached or total features evaluated indicating defect classification the process is stopped. To obtain the optimal order of the available features, the processing time for classification and the distinguishability for each feature should be evaluated. These evaluations can be performed as an off-line learning process, using the training data set. The feature-ordering scheme developed for active perception will be discussed in the section titled "Off-Line Learning". Feature ordering considers features from all available sensors, thus, fusing information from various sensors at feature level. An optimal feature ordering is performed for each pair of classes. Let there be c number of classes that need to be classified. The total number of ordered feature sets required is $c(c-1)/2$. An ordered feature set, $F_q$ represents the feature order that maximizes distinguishability between the ith and the jth classes, while keeping the processing time low. During the active perception procedure, the DOCs for all possible classes are calculated based on the evidence provided by the current features and all previous ones. If the highest DOC value is less than the prespecified threshold, the next feature is selected so that it maximizes the distinguishability between the class with the highest DOC and the one with the second highest DOC. Thus, feature ordering for an unknown object is dynamically modified on-line during the active perception process.

To start the active perception procedure, the pairwise ordered feature sets cannot be used since all the classes have an equal chance of occurring. Therefore, another feature ordering that considers the distinguishability power of a feature with respect to all the classes and its processing time is also determined. The feature out of all the available features, which is optimum in terms of distinguishability with respect to all the classes and processing time, is selected as the first feature to start the active perception processes. This feature is called the first feature. The procedure to determine the first feature will be explained in the section titled "Off-Line Learning".

Distinguishability Measure

For the active perception scheme, the features need to be ordered on the basis of their ability to distinguish between various classes. Distinguishability measure quantifies a feature's ability to differentiate between various classes by finding the area of the region in which the two classes overlap. The smaller the area, the higher the ability of the feature to distinguish between the classes.

Figure 25:
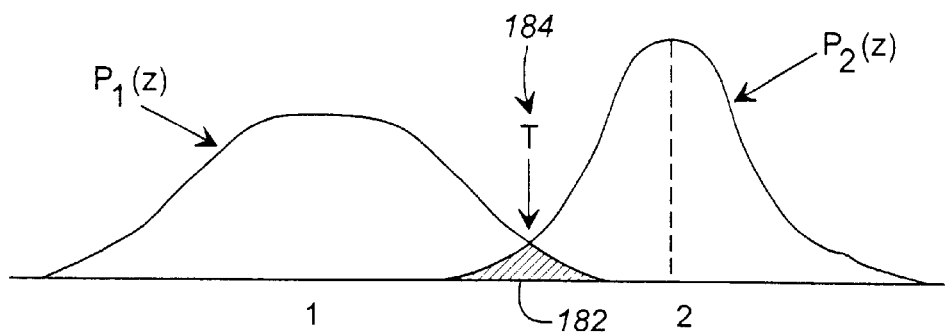
FIG. 25 illustrates the mixture probability density function of a feature for two class case.

Suppose there are two classes, $w_1$ and $w_2$, that need to be classified based on a feature A. Let there be a training data set that includes N, samples belonging to $w_1$ and $N_2$ samples belonging to $w_2$. Assuming Gaussian distribution for the training data belonging to each class (a valid assumption for a large training data set), the mixture probability density function for feature A, can be written as $$p(z) = \frac{P_1}{\sqrt{2\pi}\,\sigma_1}\exp\left(-\frac{(z-\mu_1)^2}{2\sigma_1^2}\right) + \frac{P_2}{\sqrt{2\pi}\,\sigma_2}\exp\left(-\frac{(z-\mu_2)^2}{2\sigma_2^2}\right), \quad (34)$$

where $\mu_1$ is the mean of $w_1$ training data set, $\mu_2$ is the mean of w2 training data set, a is the standard deviation about $\mu_1$, $\sigma_2$ is the standard deviation about $\mu_2$, and $P_1$ and P are the a priori probabilities of the two classes. FIG. 25 illustrates one such mixture probability density function for a feature.

Referring to FIG. 25, the shaded region 182 is the region for feature A, in which the two classes, $w_1$ and $w_2$ overlap. Let T 184 be a feature A value such that all the data points having featured A values less than T are considered belonging to class $w_1$ and all the data points having feature A values greater than or equal to T are considered belonging to class $w_2$. The probability of erroneously classifying $w_1$ data point as $w_2$ data point using feature A is $$E_A^{w_1}(T) = \int_{-\infty}^{T} \frac{1}{\sqrt{2\pi}\,\sigma_2}\exp\left(-\frac{(z-\mu_2)^2}{2\sigma_2^2}\right)dz. \quad (35)$$

Similarly, the probability of classifying a $w_2$ data point as a $w_1$ data point, using feature A is $$E_A^{w_2}(T) = \int_{T}^{\infty} \frac{1}{\sqrt{2\pi}\,\sigma_1}\exp\left(-\frac{(z-\mu_1)^2}{2\sigma_1^2}\right)dz. \quad (36)$$

Therefore, the overall probability of error, for feature A is $$E_A(T) = P_2 E_Z^{w_1}(T) + P_1 E_A^{w_2}(T) \quad (37)$$

Referring now to FIG. 25, the shaded region 182 graphically represents Equation 37. $E_A$ (T) can be considered as a distinguishability measure for feature A to differentiate between classes $w_1$ and $w_2$. Since both classes have an equal chance of occurring, the a priori probabilities are $P_1 = P_2 = 0.5$ and can be neglected in Equation 37 for comparison purposes. Thus, the distinguishability measure of feature A for classes $w_1$ and $w_2$ is $$d_A^{w1,w2} = E_A^{w1}(T) + E_A^{w2}(T), \quad (938)$$

where $E_A^{w1}$ (T) is calculated using Equation 35 and $E^{w2}{}_A$ (T) is calculated using Equation 36

Figure 26:
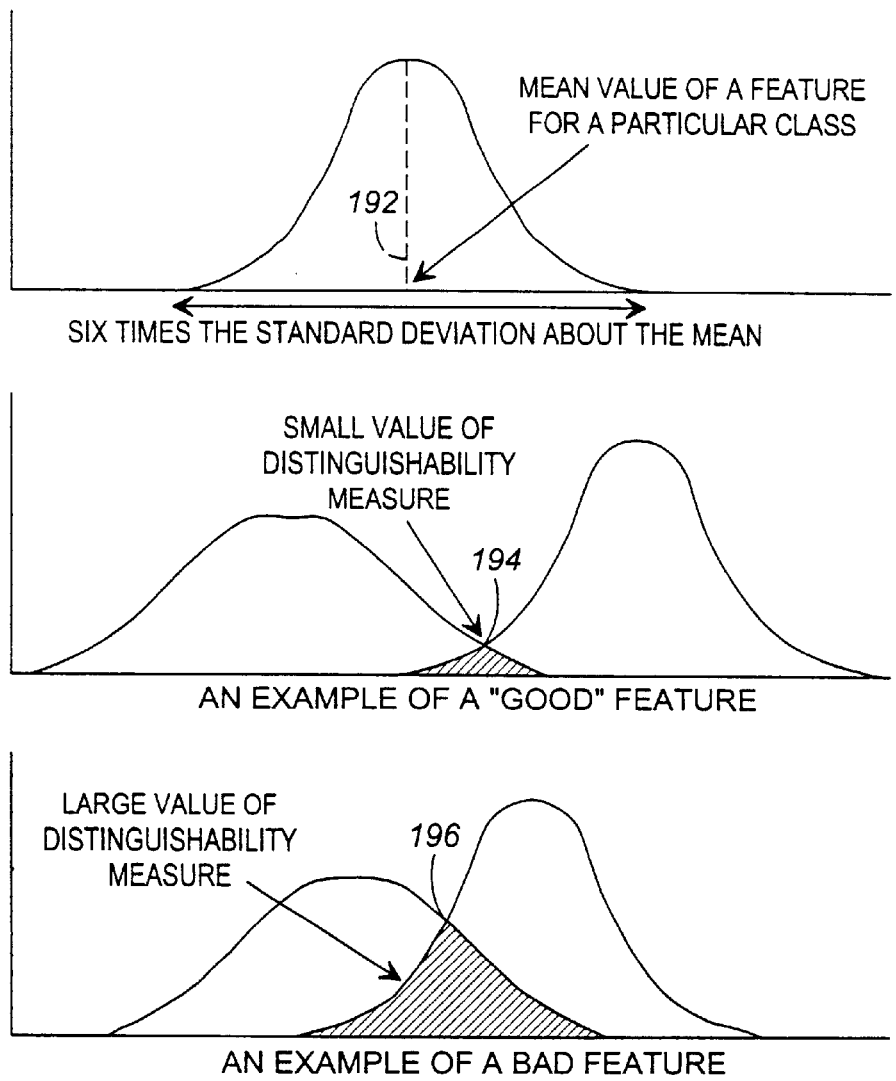
FIG. 26 illustrates the graphical representation of distinguishability measure.

FIG. 26 illustrates the feature distinguishability measure graphically. The mean value of a feature for a particular class 192 is shown. A small value of distinguishability measure is shown as shaded area 194 illustrating an example of a "good" feature, while a large value of distinguishability measure is shown as shaded area 196 illustrating an example of a "bad" feature. To calculate $d^{w1,w2}$, T needs to be determined. The value of T is determined such that $E_A$ (T) is minimal. This is done by differentiating $E_A$ (T) with respect to T and equating the result to zero. Thus, by Liebnitz's rule, we get $$\frac{1}{\sigma_1}\exp\left(-\frac{(T-\mu_1)^2}{2\sigma_1^2}\right) = \frac{1}{\sigma_2}\exp\left(-\frac{(T-\mu_2)^2}{2\sigma_2^2}\right). \quad (39)$$

Taking the natural logarithm of Equation 39 and simplifying gives the quadratic equation $$AT^2 + BT + C = 0, \quad (40)$$

where $A = \sigma_1^2 - \sigma_2^2$ $B = (\mu_1 \sigma_2^2 - \mu_2 \sigma_1^2)$ $C = \sigma_1^2 \mu_2^2 - \sigma_2^2 \mu_1^2 + 2\sigma_1^2 \sigma_2^2 \ln(\sigma_2/\sigma_1)$ Of the two possible solutions for T, the value is selected such that one of the following conditions is satisfied. The conditions are $\mu_1 < T \leq \mu_2$ $\mu_1 \leq T < \mu_2$ $\mu_2 < T \leq \mu_1$ $\mu_2 \leq T < \mu_2$ If the variances are equal, $\sigma^2 = \sigma_1^2 = \sigma_2^2$, a single solution is obtained for T that is equal to the average of the means. If the means are equal, $\mu = \mu_1 = \mu_2$, all the conditions for the selection of a single T are violated. When $\sigma_1^2 \neq \sigma_2^2$ and $\mu = \mu_1 = \mu_2$, T has two valid solutions, $T_1$ and $T_2$. The distinguishability measure, $d^{w1,w2}{}_B$ of feature B for classes $w_1$ and $w_2$ with two valid Ts is calculated as $$d_B^{w1,w2} = \frac{1}{\sqrt{2\pi}}\int_{T_1}^{T_2}\frac{1}{\sigma_1}\exp\left(-\frac{(z-\mu_1)^2}{2\sigma_1^2}\right) + \frac{1}{\sigma_2}\exp\left(-\frac{(z-\mu_2)^2}{2\sigma_2^2}\right)dz, \quad (41)$$

where $T_1 < T_2$. When $\sigma_1^2 = \sigma_2^2$ and $\mu_1 = \mu_2$, i.e., the two distributions are exactly the same, Equation 40 is understrained. For such a case, the distinguishability measure, $d_B^{w1,w2}$, of feature B for classes $w_1$ and $w_2$ is equal to 2.0, calculated by using Equation 41 with $T_1 = -$ and $T_2 = +$.

Learning

Learning is the process of acquiring knowledge. In a pattern recognition paradigm, learning is often used as a synonym for training the classification stage. R. Gonzalez and R. Woods, Digital Image Processing, Addison-Wesley Publishing Company, Reading, Mass., 1992. This learning is achieved using the training data set. In an artificial neural network paradigm, learning is defined as a process accomplished by incorporating past experiences into the interconnection weights. The learning accomplished by using the a priori information (training data set) is also called off-line learning. Learning can also be regarded as an ongoing process. Whenever new information supporting a priori knowledge is acquired, it is plausible to say the learning has been accomplished. I. Kim, A Hybrid *Analytical/Intelligent Methodology for Sensor Fusion, Doctoral Thesis*, Georgia Institute of Technology, December, 1992. This type of learning is called on-line learning.

For FINE inspection, learning is accomplished both as an off-line process and as an on-line process. The off-line learning is achieved by incorporating the a priori knowledge about the classes in terms of feature ordering for active perception. The on-line learning process fine tunes the feature ordering by aggregating the feature effectiveness calculated while performing the pattern recognition of unknown objects.

Off-Line Learning

Off-line learning is accomplished by performing the feature ordering for the active perception scheme. The training data set, which provides the a priori information about the various classes of interest, is used for the off-line learning process.

The feature ordering is performed using the distinguishability measure, previously defined in the section titled "Distinguishability Measure", and the processing time required for each feature extraction. The processing time for a feature can be determined in terms of the central processing unit (CPU) time of a computer, floating point operations per second (flops), or clock time.

Let there be N total features that are used to classify c number of classes. As mentioned previously in the section titled "Active Perception in Sensor Fusion" the total number of ordered feature sets required for c classes is $c(c-1)/2$. Let $F_{ij}$, $i=1, \ldots, c, j=i+1, \ldots, c, \neq j$, represent the ordered feature set for the ith and the jth class pair. Let $T_k$ represent the processing time required to extract the kth feature, $f_k$, where $k=1, \ldots, N$. A cost function for each feature is evaluated by considering its processing time and the distinguishability measure for classifying a class pair. Let $\gamma_k^{ij}$ be the cost function of the kth feature for the ith and the jth class pair, where $k=1, \ldots, N$, $i=1, \ldots, c$, $j=i+1, \ldots, c$, $i \neq j$. The cost function of the kth feature for class i and j is calculated as $$\gamma_k^{ij} = w_1 d_{fk}^{ij} + w_n T k, \quad (42)$$

where $w_1$, $w_2$ are weighting constants, selected such that $w_1+w_2=1$. $d_{fk}^{ij}$ represents the normalized distinguishability measure of the kth feature $f_k$ for the ith and jth class and $T_k$ represents the normalized processing time for the kth feature. $d_{Tij}$ is calculated as $$\hat{d}_{f_k}^{i,j} = \frac{d_{f_k}^{i,j}}{\max_k \{d_{f_k}^{i,j}\}}, \quad (43)$$

where $d_{fk}^{ij}$ is the distinguishability measure of the kth feature $f_k$ for the ith and the jth class and is calculated using Equation 38. The normalized processing time for the kth feature $T_k$, is calculated $$\hat{\tau}_k = \frac{\tau_k}{\max_k \{\tau_k\}}. \quad (44)$$

The cost function $\gamma_k^{ij}$ is calculated for $c(c-1)/2$ number of class pairs and for all the available features. These cost functions can be represented as a matrix $\psi$ given as $$\Psi = \begin{bmatrix} \zeta_1^{12} & \zeta_1^{13} & \cdots & \zeta_1^{1c} & \zeta_1^{23} & \cdots & \zeta_1^{2c} & \cdots & \zeta_1^{(c-1)c} \\ \zeta_2^{12} & \zeta_2^{13} & \cdots & \zeta_2^{1c} & \zeta_2^{23} & \cdots & \zeta_2^{2c} & \cdots & \zeta_2^{(c-1)c} \\ \vdots & & & & & \ddots & & & \vdots \\ \zeta_N^{12} & \zeta_N^{13} & \cdots & \zeta_N^{1c} & \zeta_N^{23} & \cdots & \zeta_N^{2c} & \cdots & \zeta_N^{(c-1)c} \end{bmatrix}. \quad (45)$$

The feature ordering $F_{ij}$ for the ith and the jth class pair is obtained by sorting the column of $\psi$, which represents cost functions for the ith and the jth class pair in ascending order. Thus, the first entry of the feature ordering $F_{ij}$ for the ith and the jth class pair is the feature $f_q$ which satisfies the following relation:

$$f_1 = \min_k \{\delta_k^{ij}\} \text{ for } k=1, \ldots, N. \quad (46)$$

To begin the active perception procedure, the first feature is required. As mentioned previously in the section titled "Active Perception in Sensor Fusion", the pairwise ordered feature sets cannot be used to initiate the active perception procedure since all the classes have an equal chance of occurring. The first feature is determined by considering its distinguishability power for all the possible class pairs and its processing time. The first feature, $f_{1st}$, is the feature whose cost function $\delta_1^{st}$, satisfies $$\zeta_{1st} = \min_k \left\{ \sum_{i=1, j=i+1}^{c} \zeta_k^{ij} \right\}, \quad k = 1, \ldots, N, \quad (47)$$

where $\delta_k^{ij}$ is the cost function calculated using Equation 42 with weighting factors $w_1=w_2=0.5$. N is the total number of available features and c is the total number of classes.

On-line Learning

On-line learning has been incorporated into the FINE inspection for adapting the active perception algorithm to the system changes by fine tuning the feature ordering obtained from the off-line learning process. A measure has been defined to monitor the system changes in terms of feature utilization. This measure is called the effectiveness of a feature.

The off-line learning process uses the training data set to determine the ordered feature sets. For defect classification, the training data set is gathered so as to provide examples of solder joints belonging to various defect classes. It is desirable that the training data set include all the possible patterns that belong to a single defect class in order to determine its correct cluster type in the feature space. In practice, the solder joint defects that are generated by the system (resulting from malfunctions or drift in control parameters) may cover a limited range of the expected feature range. Therefore, a feature that is considered bad on the basis of distinguishability measure (calculated using the training data set) may perform better under the current operating conditions of the system. Referring now to FIG. 27, a linearly misaligned surface-mounted integrated circuit (IC) has its leads 202 shifted to one side with reference to the solder pads 204 underneath. Consider the offset 206 between a solder pad centerline and an IC's lead centerline as a feature. For a 50 mil (mil is a unit used in the electronics manufacturing industry. 1 mil=1×10$^{-3}$ inch.) pitch IC, this feature may have values in the range of 0.25 mm to 1.25 mm.

However, the system may generate the linear misalignment defects with centerline offsets in the range of 0.25 mm to 0.50 mm. Thus, by monitoring the current state of system operation, the ordered feature sets may be rearranged such that the active perception process is adapted to the system's current operational state.

A learning procedure has been developed by on-line monitoring of the effectiveness of the features used by the active perception process for an unknown pattern. The effectiveness of a feature in distinguishing between two classes is determined on-line from the fuzzy partition of an unknown pattern. The effectiveness, $\eta^{ij}_k$, of the kth feature in distinguishing the ith and the ith classes is defined as $$\eta_k^{ij} = |\mu_{ij}(I) - \mu_{jk}(I)|, \quad (48)$$

where $|.|$ represents absolute operation, $\mu_{ik}(x)$ is the ith class membership of the unknown pattern x, and $\mu_{jk}(x)$ is the jth class membership of x.

The effectiveness of all the features for all the class pairs, which are employed during the active perception, is determined for a finite number of classifications. The effectiveness obtained for all the classifications is summed together and normalized for each class pair such that the maximum effectiveness becomes equal to 1.0. A new cost function $\delta_k^{ij}$ of the kth feature for the ith and the jth class pair is calculated as $$\xi_k^{ij} = w_1 \hat{\eta}_k^{i,j} + \frac{w_2}{\hat{\tau}_k}, \quad (49)$$

wherein $^2_k$, represents the normalized effectiveness of the kth feature for the ith and the jth class pair, $T_k$ is the normalized processing time for the kth feature. $w_1$ and $w_2$ are weighting factors for feature effectiveness and its processing time, respectively. The weighting factors are selected such that $w_1 + w_2 = 1.0$. The cost function $\xi$ of all the features and for all the class pairs are represented as a matrix $\Gamma$, given as $$\Gamma = \begin{bmatrix} \xi_1^{12} & \xi_1^{13} & \cdots & \xi_1^{1c} & \xi_1^{23} & \cdots & \xi_1^{2c} & \cdots & \xi_1^{(c-1)c} \\ \xi_2^{12} & \xi_2^{13} & \cdots & \xi_2^{1c} & \xi_2^{23} & \cdots & \xi_2^{2c} & \cdots & \xi_2^{(c-1)c} \\ \vdots & & & & & & & & \vdots \\ \xi_N^{12} & \xi_N^{13} & \cdots & \xi_N^{1c} & \xi_N^{23} & \cdots & \xi_N^{2c} & \cdots & \xi_N^{(c-1)c} \end{bmatrix}, \quad (50)$$

where N is the total number of available features and c is the total number of classes. The feature ordering $F_{ij}$ for the ith and the jth class pair is obtained by sorting the column of $\Gamma$, which represents cost functions for the ith and the jth class pair in descending order. Thus, the first entry of the feature ordering $F_q$ for the ith and the jth class pair is the feature $f_q$ which satisfies the following relation:

$$f_q = \max_k \{\xi_k^{ij}\} \quad \text{for } k = 1, \ldots, N. \quad (51)$$

Linear Misalignment Test

At the FINE inspection station, the linear misalignment test is triggered only if the GROSS inspection station finds a possible linearly misaligned solder joint. The linear misalignment test at the FINE inspection confirms whether the solder joints under inspection are linearly misaligned or not. Since the IR detector is insensitive to the placement defects, only vision data i.e. two-dimensional 256 gray level images, is used for linear misalignment defect classification.

The shadow free higher resolution images of the probable defective solder joints are captured using a front diffuse illumination technique. FIG. 20 illustrates an image of a typical linear misalignment defect 151. The preprocessing technique called ma scan, developed for GROSS inspection, can be applied to high resolution FINE inspection images, since the max scan is independent of the image resolution.

A max scan of the solder joints under test is calculated and compared with the max scan of good solder joints. Since the images are of high resolution, the max scan can handle noise more effectively. The noise is sometimes generated because of printed letters and traces in the processing window of max scan. A linguistic labels based fuzzy classifier is used for linear misalignment defect classification. The fuzzy classifier was explained previously in the section titled Defect Identification using Fuzzy Relations and Linguistic Variables.

Excess Solder Mass Test

The excess solder mass test is triggered at the FINE inspection station, if the IR GROSS inspection detects a solder joint with more solder mass than a good solder joint. The objective of this test module is to inspect the probable defective solder joint and to classify it into bridging, ball, or excess solder defect classes. In case of a false alarm at the GROSS inspection station, this test module should classify the solder joint as good.

This classification module uses the active perception approach to fuse vision and IR data at feature level. High resolution images of the probable defective solder joints are captured using a CCD camera. The IR thermal signature of these solder joints, captured at the GROSS inspection station, are also called upon for detailed investigation. Features are extracted from the image as well as the IR thermal signatures of the joint under test. The complete feature set available for the active perception consists of 15 vision based features and 19 IR thermal signature based features. The output of the test is the class declaration of the solder joint under test with the associated degree of certainty.

Insufficient Solder Mass Test

The insufficient solder mass test is triggered at the FINE inspection station, if the IR GROSS inspection detects a solder joint with less solder mass than a good solder joint. The objective of this test module is to inspect the probable defective solder joint and to classify it into void, insufficient, or no solder defect classes. In case of a false alarm at the GROSS inspection station, this test module should classify the solder joint as good.

This classification module uses the active perception approach to fuse vision and IR data at feature level. High resolution images of the probable defective solder joints are captured using a CCD camera. The IR thermal signature of these solder joints, captured at the GROSS inspection station, are also called upon for detailed investigation. Features are extracted from the as well as the IR thermal signatures of the joint under test. The complete feature set available for the active perception consists of 15 vision based features and 19 IR thermal signature based features. The output of the test is the class declaration of the solder joint under test with the associated degree of certainty.

Menu Driven User Interface

This section details the software developed for the prototype operation and user interface. To make the prototype use r-friendly, efforts were devoted to the development of a user-friendly interface which can be used as the basic platform for If) integrating various processing, recognition and control algorithms. The development of the user-interface facilitated the integration o f t he overall methodology for the GROSS inspection and FINE inspection.

In designing a user-friendly interface for the prototype, consideration was given to make it as simple and as self explanatory as possible. The interface developed is menu driven. When a user wishes to interact with the experimental setup, he/she is offered a list of options to select from. The menus are nested in such a way that if any menu option requires a prerequisite action, the option could not be selected until the prerequisite action has been performed. If the user selects such an option, a message directing the user to the prerequisite action is displayed on the screen. The X-Y table motion control, laser firing and image capture procedures have been embedded in the menu driven options such that they are transparent to the user. If a selected option require X-Y table motion and image capture, it is performed automatically. The training phase for a new PCB for inspection has been developed such that it reduces to simple mouse driven and/or arrow keys operation. The software for the interface has been developed using C computer language. The programming has been done in a modular fashion so that adding new menus or new options to existing menu do not require any modification of the existing menus. FIG. 28 illustrates a menu screen developed for the prototype.

Results

A set of five GVC Ethernet cards were purchased and a number of defects were created at the U.S Army Missile Command soldering facility at Huntsville, Ala. The algorithms developed for GROSS inspection and FINE inspection were tested on these PCBs.

GROSS Inspection Results

The perceptron classifier for the component presence test gave 100% correct classification results. The classifier is very reliable and robust to shadow side window placement and the angle of illumination. The linear misalignment and angular misalignment test did not miss any existing defects, but for some PCBs they had a false alarm of 3% to 4%. The false alarms were created because of the printed letters and traces in the processing window. These printed letters and traces appear as bright spots in the processing windows. To avoid the false alarms, the processing windows need to be defined carefully. This requirement makes these test procedures sensitive to the window location. The processing time for the vision GROSS inspection, depending upon the number of processing windows and their sizes ranging from 0.7 seconds to 1.5 seconds.

The perceptron classifier for the IR GROSS inspection detected all the defective solder joints and classified them correctly into excess solder mass category or insufficient solder mass category. The IR GROSS inspection had a false alarm of 2%. The false alarms were created because of the high sensitivity of InSb sensor to the surface profile of the solder joint. If the surface of the solder joint is contaminated with dust particles or flux, the InSb sensor may not detect any signal at all. The MCT sensor is not sensitive to these variations.

FINE Inspection Results

The linear misalignment test module at the FINE inspection station classified all the linearly misaligned solder joints correctly. The satisfactory performance of this module illustrates that max scan is independent of the image resolution and can be effectively applied at various resolution levels.

Figure 29:
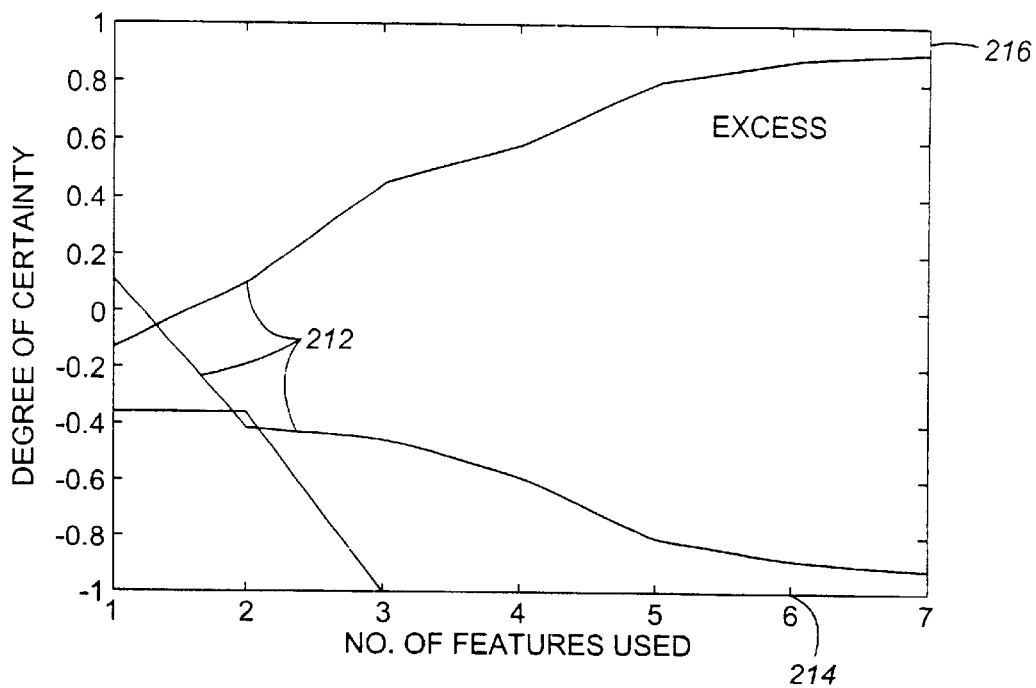
FIG. 29 illustrates DOC trajectories for an excess solder defect.

The excess solder mass test module was tested using 52 solder joints belonging to good, excess solder, bridging, and ball classes. The DOC threshold was set to 0.90. The active perception approach to classification misclassified one excess solder joint as bridging defect. The remaining 51 solder joints were classified correctly. The application of active perception allowed the classification of defects to be performed using a subset of the 38 feature set. FIG. 29 illustrates the DOC trajectories 212 obtained for an excess solder defect classification using the active perception approach. Note that the classification is performed using only six features 214 with a DOC of 0.915 216.

Figure 30:
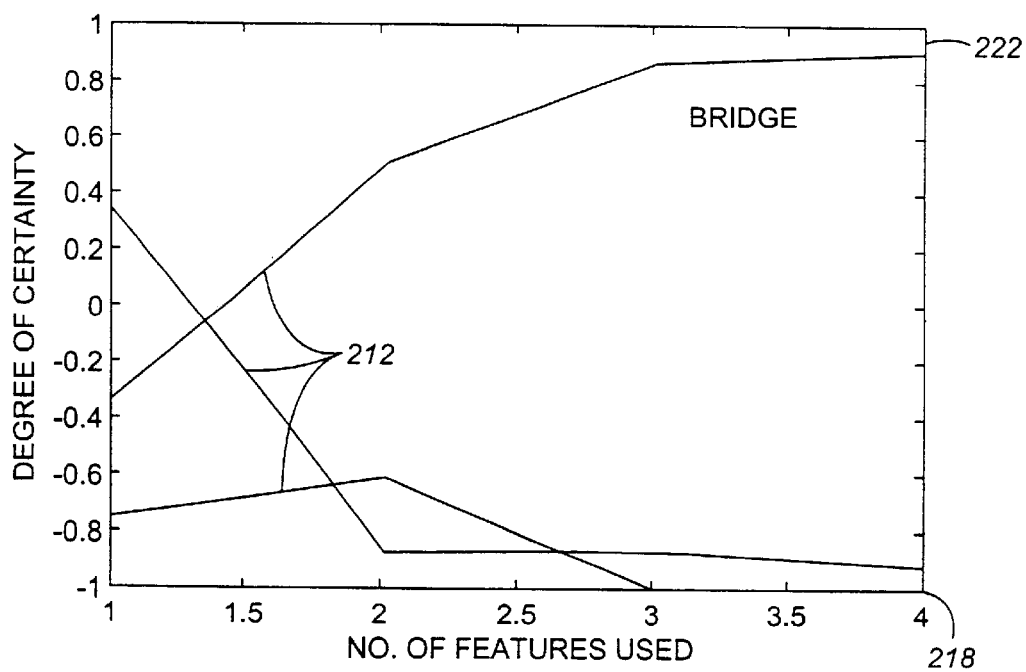
FIG. 30 illustrates DOC trajectories for a bridging defect.

FIG. 30 illustrates DOC trajectories 212 obtained for a bridging defect classification. For this case, only four features 218 were used and the associated DOC is 0.920 222.

Figure 31:
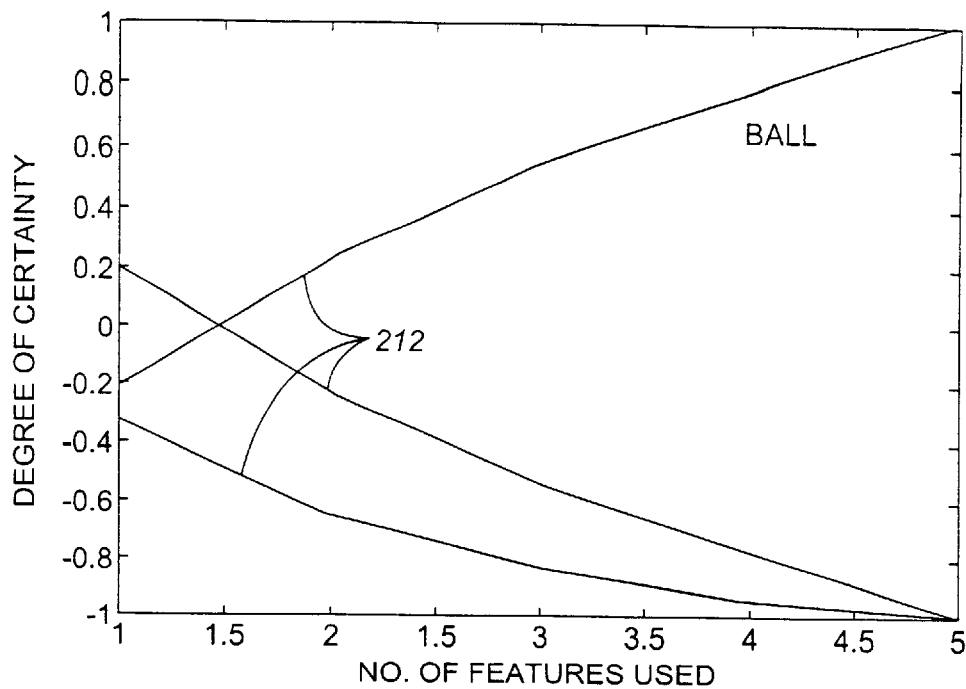
FIG. 31 illustrates DOC trajectories for a solder ball defect.

FIG. 31 illustrates the DOC trajectories 212 obtained for a solder ball defect classification.

Figure 32:
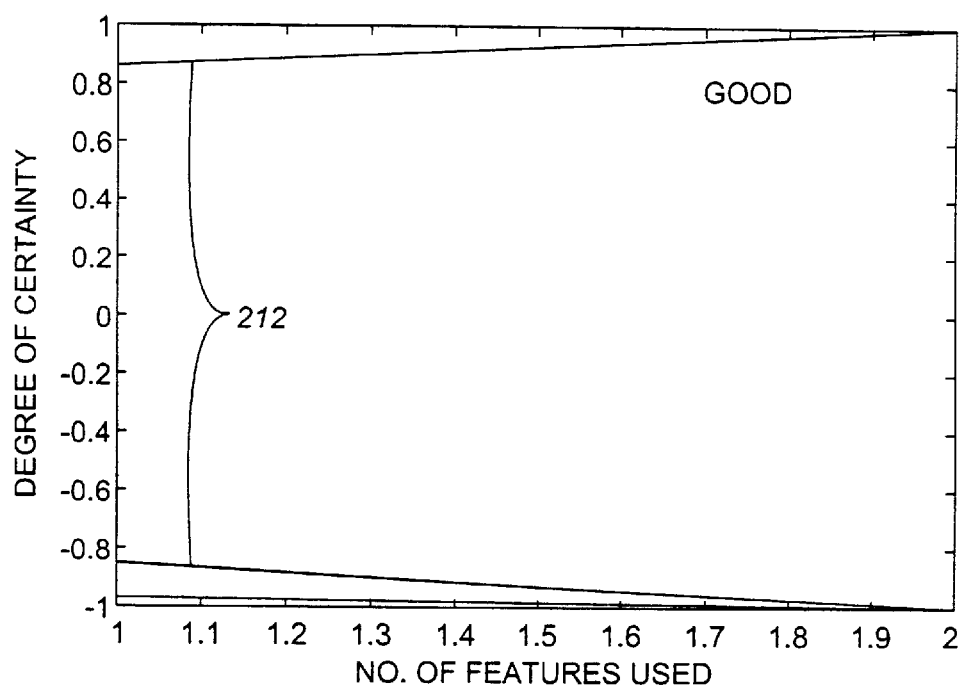
FIG. 32 illustrates DOC trajectories for a good solder joint.

This test module also classified the good solder joints correctly. FIG. 32 illustrates the DOC trajectories 212 obtained for a good solder joint classification.

Figure 33:
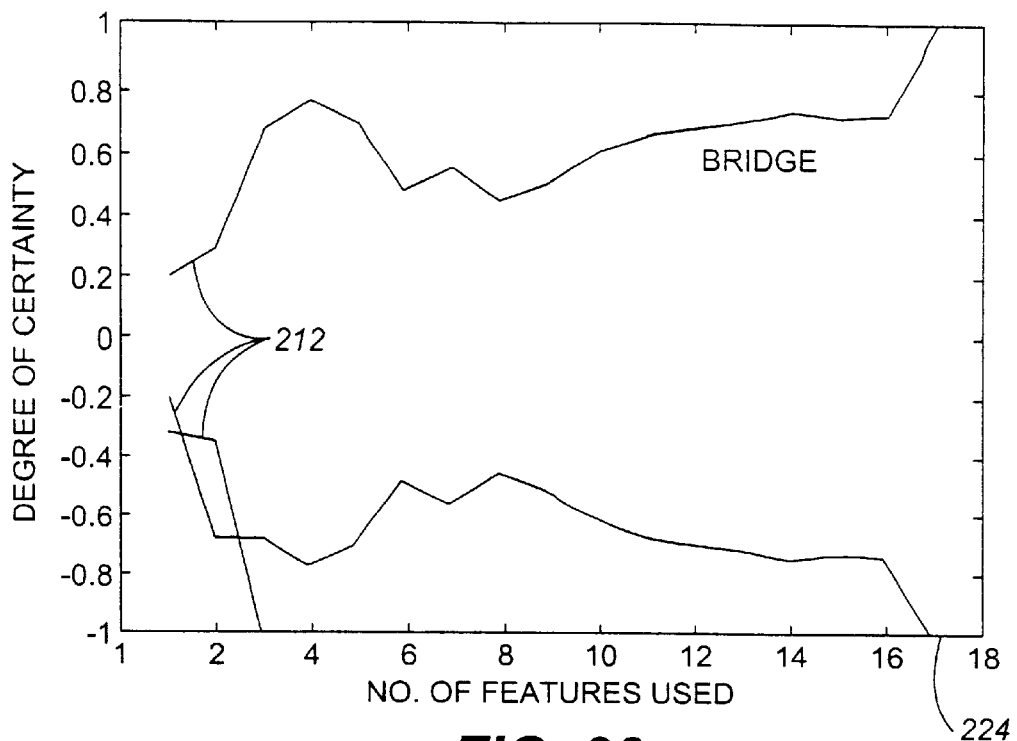
FIG. 33 illustrates DOC trajectories for a bridging defect.

The active perception scheme aggregates the evidence obtained from each feature until the specified degree of certainty is obtained. This means that for borderline defect cases between defect classes, more features are used as compared to the typical defects. FIG. 33 illustrates the DOC trajectories 212 obtained for a bridging defect using 17 features 224 out of an available 38.

The classification of 52 solder joints, by the excess solder mass test module, was performed using 139 features which is 7% of the total available features.

Figure 34:
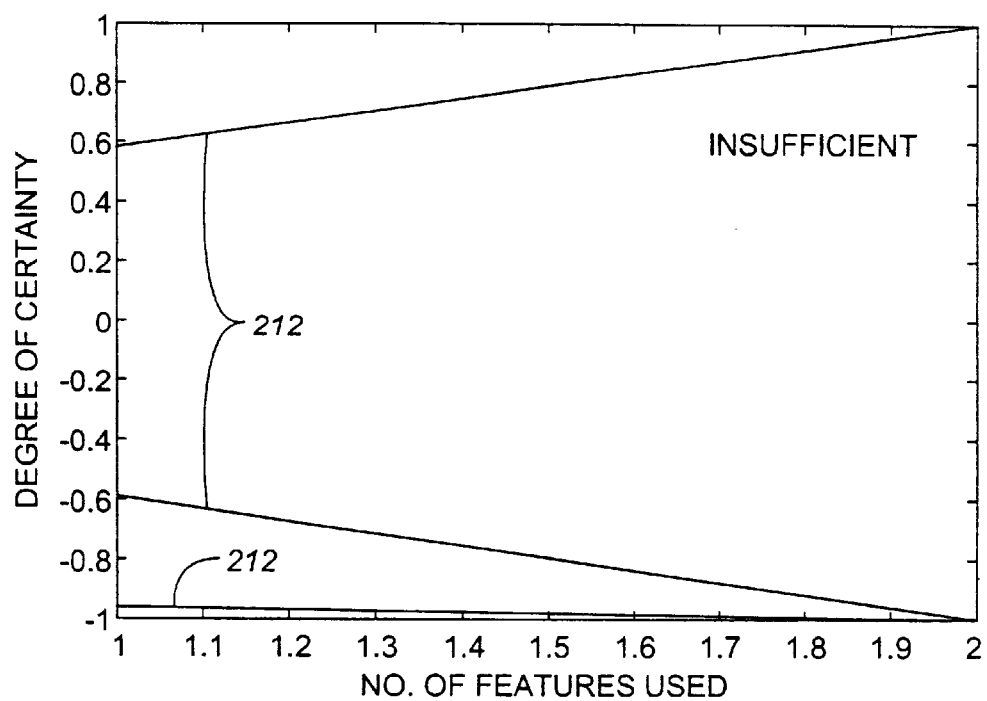
FIG. 34 illustrates DOC trajectories for an insufficient solder defect.
Figure 35:
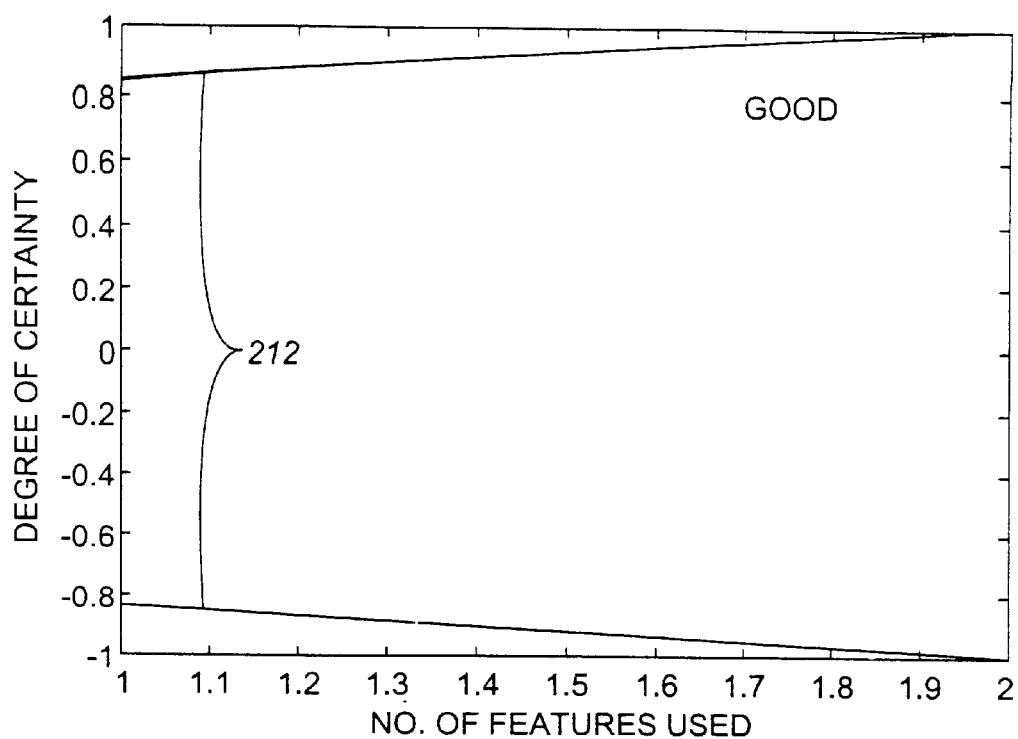
FIG. 35 illustrates DOC trajectories for a good solder joint.

The insufficient solder mass test module was tested using 41 solder joints belonging to good, insufficient, and no solder classes. The DOC threshold was set to 0.90. The module gave 100% results. The 41 solder joints were classified using 78 features which is 5% of the total available features. FIG. 34 and FIG. 35 show the DOC trajectories 212 obtained by the insufficient solder mass test, for an insufficient solder defect and a good solder joint, respectively.

The FINE inspection results show that the active perception scheme using sensor fusion at feature level not only performs the classification with a fewer number of features (which implies less processing time), but also provides an index of confidence associated with the classification.

It is to be understood that the foregoing is descriptive of an illustrative, preferred embodiment of the invention. Numerous variations or changes may occur to those skilled in the art without departure from the spirit and scope of the invention.

What is claimed is:

1. A method for inspecting circuits by performing feature level sensor fusion using an active perception process, comprising the steps of:

using a gross inspection station to determine global circuit features and rapidly detect defects in the global circuit features, the gross inspection station configured to receive data from at least two infrared (IR) sensors and a vision sensor, using a fine inspection station to generate local circuit features, fusing the local circuit features using active perception;

performing data level sensor fusion at the gross inspection station by determining a ratio of the outputs of the two IR sensors thus canceling effectively the effect of sensor emissivity and improving data reliability;

using an off-line learning process at the gross inspection station, the off-line learning process configured to perform feature ordering for active perception, the feature ordering performed using a distinguishability measure and the processing time required to extract each feature;

evaluating a cost function for each feature;

using a perceptron classifier at the gross inspection station to classify defects;

computing a degree of certainty index at the gross inspection station the degree of certainty index representing a confidence level associated with a classification result;

performing feature level sensor fusion at the fine inspection station using an active perception process, the active perception process configured to fuse information from the IR and vision sensors and also configured to minimize the processing time by controlling the information gathering process by aligning features optimally so that features requiring less processing time and providing greater distinguishability between failure classes are listed first in the ordering scheme;

using an on-line learning process at the fine inspection station, the on-line learning process configured to adapt the active perception process to changes and disturbances by fine tuning the feature ordering; and monitoring the system changes and disturbances using a measure called feature effectiveness that optimizes on-line the feature utilization in the classification task.

2. The method as defined in claim 1, further comprising the step of teaching the defects to the active perception process using an off-line learning process using a training data set.

3. The method as defined in claim 1, further comprising the step of teaching feature defects to the active perception process using an on-line learning process where, by monitoring the current state of system operation, the feature defects are rearranged such that the active perception process is adapted to the system's current operational state.

4. The method as defined in claim 1, further comprising the step of ordering each of the features based upon their ability to distinguish between different defect classes.

5. The method as defined in claim 4, further comprising the step of quantifying the ability of each of the features to distinguish between different defect classes by determining an area of a defect region in which different defect classes overlap.

6. A system for inspecting circuits by performing feature level sensor fusion using an active perception process, comprising:

means for determining global circuit features and rapidly detecting defects in the global circuit features, the determining means configured to receive data from at least two infrared (IR) sensors and a vision sensor;

means for generating local circuit features;

means for fusing the local circuit features using active perception;

means for performing data level sensor fusion at the gross inspection station by determining a ratio of the outputs of the two IR sensors thus canceling effectively the effect of sensor emissivity and improving data reliability;

means for performing an off-line learning process at the gross inspection station, the off-line learning process configured to perform feature ordering for active perception the feature ordering performed using a distinguishability measure and the processing time required to extract each feature;

means for evaluating a cost function for each feature;

means for classifying defects using a perceptron classifier at the gross inspection station;

means for computing a degree of certainty index at the gross inspection station the degree of certainty index representing a confidence level associated with a classification result;

means for performing feature level sensor fusion at the fine inspection station using an active perception process, the active perception process configured to fuse information from the IR and vision sensors and also configured to minimize the processing time by controlling the information gathering process by aligning features optimally so that features requiring less processing time and providing greater distinguishability between failure classes are listed first in the ordering scheme, means for using an on-line learning process at the fine inspection station the on-line learning process configured to adapt the active perception process to changes and disturbances by fine tuning the feature ordering; and means for monitoring the system changes and disturbances using a measure called feature effectiveness that optimizes on-line the feature utilization in the classification task.

7. The system as defined in claim 6, further comprising means for teaching the defects to the active perception process using an off-line learning process using a training data set.

8. The system as defined in claim 6, further comprising means for teaching the defects to the active perception process using an on-line learning process where, by monitoring the current state of system operation, the feature defects are rearranged such that the active perception process is adapted to the system's current operational state.

9. The system as defined in claim 6, further comprising means for ordering each of the features based upon their ability to distinguish between different defect classes.

10. The system as defined in claim 9, further comprising means for quantifying the ability of each of the features to distinguish between the different defect classes by determining an area of a defect region in which the different defect classes overlap.

11. A computer readable medium having a program for inspecting circuits by performing feature level sensor fusion using an active perception process the medium comprising logic for performing the steps of:

using a gross inspection station to determine global circuit features and rapidly detect defects in the global circuit features the gross inspection station configured to receive data from at least two infrared (R) sensors and a vision sensor;

using a fine inspection station to generate local circuit features;

fusing the local circuit features using active perception;

performing data level sensor fusion at the gross inspection station by determining a ratio of the outputs of the two IR sensors, thus canceling effectively the effect of sensor emissivity and improving data reliability;

using an off-line learning process at the gross inspection station the off-line learning process configured to perform feature ordering for active perception, the feature ordering performed using a distinguishability measure and the processing time required to extract each feature;

evaluating a cost function for each feature;

using a perceptron classifier at the gross inspection station to classify defects;

computing a degree of certainty index at the gross inspection station, the degree of certainty index representing a confidence level associated with a classification result;

performing feature level sensor fusion at the fine inspection station using an active perception process, the active perception process configured to fuse information from the IR and vision sensors and also configured to minimize the processing time by controlling the information gathering process by aligning features optimally so that features requiring less processing time and providing greater distinguishability between failure classes are listed first in the ordering scheme;

using an on-line learning process at the fine inspection station, the on-line learning process configured to adapt the active perception process to changes and disturbances by fine tuning the feature ordering; and monitoring the system changes and disturbances using a measure called feature effectiveness that optimizes on-line the feature utilization in the classification task.

12. The program as defined in claim 11, further comprising logic for performing the step of teaching the defect classes to the active perception process using an off-line learning process using a training data set.

13. The program as defined in claim 11, further comprising logic for performing the step of teaching feature defects to the active perception process using an on-line learning process where, by monitoring the current state of system operation, the feature defects are rearranged such that the active perception process is adapted to the system's current operational state.

14. The program as defined in claim 11, further comprising logic for performing the step of ordering each of the features based upon their ability to distinguish between different defect classes.

15. The program as defined in claim 14, further comprising logic for performing the step of quantifying the ability of each of the features to distinguish between different defect classes by determining an area of a defect region in which different defect classes overlap.

* * * * *